(12) United States Patent
LaBelle et al.

(10) Patent No.: US 11,714,083 B2
(45) Date of Patent: Aug. 1, 2023

(54) POINT-OF-CARE APPARATUS AND METHODS FOR ANALYTE DETECTIONS USING ELECTROCHEMICAL IMPEDANCE OR CAPACITANCE

(71) Applicants: Arizona Board of Regents on behalf of Arizona State University, Scottsdale, AZ (US); MAYO FOUNDATION FOR MEDICAL EDUCATION AND RESEARCH, Rochester, MN (US); AXIM Biotechnologies, Inc., New York, NY (US)

(72) Inventors: Jeffrey LaBelle, Tempe, AZ (US); Garrett Repp, Tempe, AZ (US); Chi Lin, Tempe, AZ (US); Mark Spano, Casa Grande, AZ (US); Jennifer Blain Christen, Chandler, AZ (US); Hongwu Jiang, Chandler, AZ (US); Marcus Smith, Birmingham, AL (US); Andrew Penman, Birmingham, AL (US); Pierce Youngbar, Birmingham, AL (US); Mackenzie Honikel, Chandler, AZ (US); Curtiss Cook, Scottsdale, AZ (US)

(73) Assignees: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US); AXIM BIOTECHNOLOGIES. INC., New York, NY (US)

( * ) Notice: Subject to any disclaimer, the term of this patent is extended or adjusted under 35 U.S.C. 154(b) by 538 days.

(21) Appl. No.: 16/612,270

(22) PCT Filed: May 4, 2018

(86) PCT No.: PCT/US2018/031160
§ 371 (c)(1),
(2) Date: Nov. 8, 2019

(87) PCT Pub. No.: WO2018/208610
PCT Pub. Date: Nov. 15, 2018

(65) Prior Publication Data
US 2021/0223196 A1    Jul. 22, 2021

Related U.S. Application Data

(60) Provisional application No. 62/505,004, filed on May 11, 2017.

(51) Int. Cl.
*G01N 33/543*    (2006.01)
*G01N 27/02*    (2006.01)
(Continued)

(52) U.S. Cl.
CPC ....... *G01N 33/5438* (2013.01); *G01N 27/026* (2013.01); *G01N 27/3276* (2013.01);
(Continued)

(58) Field of Classification Search
CPC .................................................. G01N 33/5438
See application file for complete search history.

(56) References Cited

U.S. PATENT DOCUMENTS

| 2010/0069253 A1 | 3/2010 | Gindilis |
| 2010/0169035 A1 | 7/2010 | Liang |

(Continued)

FOREIGN PATENT DOCUMENTS

| WO | 2016025153 A1 | 2/2016 |
| WO | 2017196860 A1 | 11/2017 |

OTHER PUBLICATIONS

Pournaras et al., Development of an impedimetric immunosensor based on electropolymerized polytyramine films for the direct detection of *Salmonella typhimurium* in pure cultures of type strains and inoculated real samples, 2008, Analytics Chimica Acta, vol. 624, pp. 301-307. (Year: 2008).*

(Continued)

*Primary Examiner* — Melanie Brown
(74) *Attorney, Agent, or Firm* — Quarles & Brady LLP

(57) ABSTRACT

The presence of analytes can be detected in the bodily fluid using Electrochemical Impedance Spectroscopy (EIS) or Electrochemical Capacitance Spectroscopy (ECS) in devices, such as handheld point-of-care devices. The devices, as well as systems and methods, utilize using Electrochemical Impedance Spectroscopy (EIS) or Electrochemical Capacitance Spectroscopy (EIS) in combination with an antibody or other target-capturing molecule on a working electrode. Imaginary impedance or phase shift, as well as background subtraction, also may be utilized.

11 Claims, 17 Drawing Sheets

(51) Int. Cl.
    *G01N 27/327* (2006.01)
    *G01N 33/487* (2006.01)
    *G01N 33/53* (2006.01)
    *G01N 33/569* (2006.01)
    *G01N 33/66* (2006.01)
    *G01N 35/00* (2006.01)
(52) U.S. Cl.
    CPC ... *G01N 33/48707* (2013.01); *G01N 33/5308* (2013.01); *G01N 33/56983* (2013.01); *G01N 33/66* (2013.01); *G01N 35/00029* (2013.01); *G01N 2333/075* (2013.01)

(56) References Cited

U.S. PATENT DOCUMENTS

| | | | |
|---|---|---|---|
| 2011/0201099 A1* | 8/2011 | Anderson | B29C 48/266 422/68.1 |
| 2013/0328573 A1 | 12/2013 | Yang | |
| 2014/0273187 A1* | 9/2014 | Johnson | G01N 33/5438 435/287.2 |
| 2017/0059561 A1* | 3/2017 | Bhansali | G01N 33/5438 |

OTHER PUBLICATIONS

Ramanaviciene et al., Capacitive micromachined ultrasound transducer for immunosensor design, 2010, Analyst, vol. 135, pp. 1531-1534. (Year: 2010).*
Virzonis et al., Resonant gravimetric immunosensing based on capacitive micromachined ultrasound transducers, Microchim Acta, 2014, vol. 181, pp. 1749-1757. (Year: 2014).*
Liu et al., Detection of complement C1-inhibitor with a piezoelectric immunosensor, Fresnius Journal of Analytical Chemistry, 2001, vol. 369, pp. 483-485. (Year: 2001).*
Adamson, T. L. et al. Detection of 1,5-Anhydroglucitol by Electrochemical Impedance Spectroscopy. J. Diabetes Sci. Technol. 2014, 8 (2), 350-355.
Adamson, T. L. et al. The Promise of Electrochemical Impedance Spectroscopy as Novel Technology for the Management of Patients with Diabetes Mellitus. Analyst 2012, 137 (18), 4179-4187.
Baudouin, C. et al. Correlation between Tear IgE Levels and HLA-DR Expression by Conjunctival Cells in Allergic and Nonallergic Chronic Conjunctivitis. Graefe's Arch. Clin. Exp. Ophthalmol. 2000, 238 (11), 900-904.
Beckman, K. A. et al. Making the Diagnosis of Sjogren's Syndrome in Patients with Dry Eye. Clin. Ophthalmol. 2015, 10, 43.
Boonyasit, Y. et al. A Multiplexed Three-Dimensional Paper-Based Electrochemical Impedance Device for Simultaneous Label-Free Affinity Sensing of Total and Glycated Haemoglobin: The Potential of Using a Specific Single-Frequency Value for Analysis. Anal. Chim. Acta 2016, 936, 1-11.
Cardinell, B. A. et al. Enzymatic Detection of Traumatic Brain Injury Related Biomarkers. Methods Mol. Biol. 2017, 1572, 89-112.
Chin, C. D. et al. Commercialization of Microfluidic Point-of-Care Diagnostic Devices. Lab Chip 2012, 12 (12), 2118-2134.
D'Souza, S. et al. Practical Issues Concerning Tear Protein Assays in Dry Eye. Eye Vis. 2014, 1 (1), 6.
Dumortier, G. et al. Lachrymal Determinations: Methods and Updates on Biopharmaceutical and Clinical Applications. Ophthalmic Res. 2004, 36 (4), 183-194.
Esfandyarpour, R. et al. Nanoelectronic Three-Dimensional (3D) Nanotip Sensing Array for Real-Time, Sensitive, Label-Free Sequence Specific Detection of Nucleic Acids. Biomed. Microdevices 2016, 18 (1), 7.
Fomo, G. et al. Aptameric Recognition Modulated Electroactivity of Poly (4-Styrenesolfonic Acid)-Doped Polyaniline Films for Single-Shot Detection of Tetrodotoxin. Sensors 2015, 15 (9), 22547-22560.
Food and Drug Administration 66 FR 28526—Guidance for Industry on Bioanalytical Method Validation; Federal Register vol. 66, Issue 100 (May 23, 2001).
Fujishima, H. et al. Allergic Conjunctivitis and Dry Eye. Br. J. Ophthalmol. 1996, 80 (11), 994-997.
German, N. et al. The Use of Different Glucose Oxidases for the Development of an Amperometric Reagentless Glucose Biosensor Based on Gold Nanoparticles Covered by Polypyrrole. Electrochim. Acta 2015, 169, 326-333.
Hagan, S. et al. Tear Fluid Biomarkers in Ocular and Systemic Disease: Potential Use for Predictive, Preventive and Personalised Medicine. EPMA J. 2016, 7, 1 DOI: 10.1186/s13167-016-0065-3.
Halade, G. V. et al. Matrix Metalloproteinase (MMP)-9: A Proximal Biomarker for Cardiac Remodeling and a Distal Biomarker for Inflammation. Pharmacol. Ther. 2013, 139 (1), 32-40.
Hamilton, R. G. Accuracy of US Food and Drug Administration-cleared IgE Antibody Assays in the Presence of Anti-IgE (Omalizumab). J. Allergy Clin. Immunol. 2006, 117 (4), 759-766.
Hernandez, K. et al. Control of Protein Immobilization: Coupling Immobilization and Site-Directed Mutagenesis to Improve Biocatalyst or Biosensor Performance. Enzyme Microb. Technol. 2011, 48 (2), 107-122.
Hom, M. M. et al. Allergic Conjunctivitis and Dry Eye Syndrome. Ann. Allergy, Asthma, Immunol. 2012, 108 (3), 163-166.
International Searching Authority, International Search Report and Written Opinion for application PCT/US2018/031160. dated Jul. 23, 2018.
Kreuzer, M. et al. Development of an Immunosensor for the Determination of Allergy Antibody (IgE) in Blood Samples. Anal. Chim. Acta 2001, 442 (1), 45-53.
La Belle, J. T. et al. Development of a Novel Single Sensor Multiplexed Marker Assay. Analyst 2011, 136 (7), 1496-1501.
La Rosa, M. et al. Allergic Conjunctivitis: A Comprehensive Review of the Literature. Ital. J. Pediatr. 2013, 39 (1), 18.
Lemp, M. A. et al. Tear Osmolarity in the Diagnosis and Management of Dry Eye Disease. Am. J. Ophthalmol. 2011, 151 (5), 792-798.
Leonardi, A. et al. Ocular Allergy: Recognizing and Diagnosing Hypersensitivity Disorders of the Ocular Surface. Allergy 2012, 67 (11), 1327-1337.
Lin, C. et al. Feasibility in the Development of a Multi-Marker Detection Platform. Biosens. Bioelectron. 2017, 89, 743-749.
Luo, X., et al. "Ultrasensitive label free electrical detection of insulin in neat blood serum." Analytical chemistry 85.8 (2013): 4129-4134.
Makaraviciute, A. et al. Site-Directed Antibody Immobilization Techniques for Immunosensors. Biosens. Bioelectron. 2013, 50, 460-471.

(56) References Cited

OTHER PUBLICATIONS

Malvano, F., et al. "Impedimetric label-free immunosensor on disposable modified screen-printed electrodes for ochratoxin A." Biosensors 6.3 (2016): 33.

Manaviat, M. R. et al. Prevalence of Dry Eye Syndrome and Diabetic Retinopathy in Type 2 Diabetic Patients. BMC Ophthalmol. 2008, 8(1), 10.

Marques, M. R. et al. Simulated Biological Fluids with Possible Application in Dissolution Testing. Dissolution Technol. 2011, 18 (3), 15-28.

Mattos, A. et al. A Dual Quartz Crystal Microbalance for Human Cardiac Troponin T in Real Time Detection. Sens. Actuators, B 2012, 161 (1), 439-446.

Miller, Y. I. et al. Kinetics of Hemin Distribution in Plasma Reveals Its Role in Lipoprotein Oxidation. Biochim. Biophys. Acta, Mol. Basis Dis. 1999, 1454 (2), 153-164.

Olokoba, A. B. et al. Type 2 Diabetes Mellitus: A Review of Current Trends. Oman Med. J. 2012, 27 (4), 269-273.

Olson, W. C. et al. Dissociation Kinetics of Antigen-Antibody Interactions: Studies on a Panel of Anti-Albumin Monoclonal Antibodies. Mol. Immunol. 1989, 26 (2), 129-136.

Ozcan, B. et al. Introducing a New Method for Evaluation of the Interaction between an Antigen and an Antibody: Single Frequency Impedance Analysis for Biosensing Systems. Talanta 2014, 125, 7-13.

Pandolfi, M. et al. A Histochemical Study of the Fibrinolytic Activity: Cornea, Conjunctiva, and Lacrimal Gland. Arch. Ophthalmol. 1967, 77 (2), 258-264.

Patil, A. V. et al. Immittance Electroanalysis in Diagnostics. Anal. Chem. 2015, 87 (2), 944-950.

Posa, A. et al. Schirmer Strip vs. Capillary Tube Method: Non-Invasive Methods of Obtaining Proteins from Tear Fluid. Ann. Anat. 2013, 195 (2), 137-142.

Rosario, N. et al. Epidemiology of Allergic Conjunctivitis. Curr. Opin. Allergy Clin. Immunol. 2011, 11 (5), 471-476.

Roy, N. S. et al. The Growing Need for Validated Biomarkers and Endpoints for Dry Eye Clinical ResearchBiomarkers and Endpoints in Dry Eye Clinical Research. Invest. Ophthalmol. Visual Sci. 2017, 58 (6), BIO1-BIO19.

Savini, G. et al. The Challenge of Dry Eye Diagnosis. Clin. Ophthalmol. 2008, 2 (1), 31-55.

Small, D. et al. Comparison of Tear Sampling Techniques for Pharmacokinetic Analysis: Ofloxacin Concentrations in Rabbit Tears after Sampling with Schirmer Tear Strips, Capillary Tubes, or Surgical Sponges. J. Ocul. Pharmacol. Ther. 2000, 16 (5), 439-446.

Stull, C. et al. The Prevalence and Characteristics of Chronic Ocular Itch: A Cross-Sectional Survey. Itch 2017, 2 (1), e4.

Su, X. et al. Self-Assembled Monolayer-Based Piezoelectric Crystal Immunosensor for the Quantification of Total Human Immunoglobulin E. Anal. Biochem. 1999, 273 (1), 66-72.

Van Berkel, P. H. et al. Characterization of Monoclonal Antibodies against Human Lactoferrin. J. Immunol. Methods 2002, 267 (2), 139-150.

Van Setten, G.-B. et al. Effects of the Schirmer Test on the Fibrinolytic System in the Tear Fluid. Exp. Eye Res. 1990, 50 (2), 135-141.

Xiao, Y. et al. Enzyme-Linked Immunosorbent Assay (ELISA) and Blocking with Bovine Serum Albumin (BSA)?not All BSAs Are Alike. J. Immunol. Methods 2012, 384 (1), 148-151.

Yamada, K. et al. Distance-Based Tear Lactoferrin Assay on Microfluidic Paper Device Using Interfacial Interactions on Surface-Modified Cellulose. ACS Appl. Mater. Interfaces 2015, 7 (44), 24864-24875.

* cited by examiner

| DIMENSION (mm) | SURFACE AREA (mm^2) | EST. VOLUME CAPTURED (L) | %RSD |
|---|---|---|---|
| 1.5x1.5 | 2.25 | 0.331336 | 16% |
| 2x2 | 4 | 0.684438 | 20% |
| 2.5x2.5 | 6.25 | 0.992855 | 7% |
| 3x3 | 9 | 1.466901 | 12% |

FIG. 7

| FREQ (Hz) | LACTOFERRIN SENSORS | | | | | BLANK SENSORS | | | | |
|---|---|---|---|---|---|---|---|---|---|---|
| | e12 | f3 | e10 | AVG | %RSD | %CHANGE | FREQ (Hz) | f6 | E6 | e5 | AVG | %RSD |
| 97.66 | -3841 | -4618 | -4100 | -4186 | 9% | 14% | 97.66 | -3632 | -3774 | -3591 | -3666 | 3% |
| 81.38 | -4131 | -5033 | -4419 | -4528 | 10% | 19% | 81.38 | -3721 | -3889 | -3760 | -3790 | 2% |
| 69.75 | -4336 | -5339 | -4651 | -4775 | 11% | 25% | 69.75 | -3698 | -3892 | -3828 | -3806 | 3% |
| 57.44 | -4444 | -5517 | -4780 | -4914 | 11% | 32% | 57.44 | -3573 | -3791 | -3794 | -3719 | 3% |
| 46.50 | -4458 | -5569 | -4800 | -4942 | 12% | 39% | 46.50 | -3373 | -3613 | -3677 | -3554 | 5% |
| 37.56 | -4382 | -5495 | -4715 | -4864 | 12% | 46% | 37.56 | -3124 | -3386 | -3497 | -3336 | 6% |
| 31.50 | -4232 | -5301 | -4541 | -4691 | 12% | 52% | 31.50 | -2856 | -3131 | -3279 | -3089 | 7% |
| 25.70 | -4020 | -5020 | -4302 | -4447 | 12% | 57% | 25.70 | -2585 | -2874 | -3046 | -2835 | 8% |
| 21.23 | -3768 | -4684 | -4019 | -4157 | 11% | 61% | 21.23 | -2323 | -2620 | -2813 | -2585 | 10% |
| 17.44 | -3503 | -4318 | -3720 | -3847 | 11% | 63% | 17.44 | -2081 | -2386 | -2595 | -2353 | 11% |
| MIN | -4458 | -5569 | -4800 | -4942 | 12% | 30% | MIN | -3721 | -3892 | -3828 | -3806 | 2% |
| PEAK FREQ | 46.50 | 46.50 | 46.50 | 46.50 | 0% | | PEAK FREQ | 81.38 | 69.75 | 69.75 | 46.50 | 0% |

FIG. 8

| FREQ (Hz) | LACTOFERRIN SENSORS | | | | | BLANK SENSORS | | | | |
|---|---|---|---|---|---|---|---|---|---|---|
| | e12 | f3 | e10 | AVG | %RSD | %CHANGE | FREQ (Hz) | f6 | E6 | e5 | AVG | %RSD |
| 97.66 | -49.3 | -53.0 | -51.0 | -51.1 | 4% | 21% | 97.66 | -42.6 | -42.3 | -44.5 | -43.1 | 3% |
| 81.38 | -46.4 | -49.9 | -47.8 | -48.0 | 4% | 23% | 81.38 | -39.0 | -38.9 | -41.3 | -39.7 | 3% |
| 69.75 | -43.1 | -46.2 | -44.4 | -44.6 | 3% | 27% | 69.75 | -35.1 | -35.2 | -37.8 | -36.0 | 4% |
| 57.44 | -39.6 | -42.3 | -40.7 | -40.9 | 3% | 29% | 57.44 | -31.3 | -31.6 | -34.2 | -32.4 | 5% |
| 46.50 | -36.0 | -38.3 | -37.0 | -37.1 | 3% | 33% | 46.50 | -27.6 | -28.0 | -30.7 | -28.8 | 6% |
| 37.56 | -32.6 | -34.5 | -33.4 | -33.5 | 3% | 35% | 37.56 | -24.2 | -24.8 | -27.3 | -25.4 | 6% |
| 31.50 | -29.3 | -30.8 | -30.0 | -30.0 | 2% | 37% | 31.50 | -21.2 | -21.9 | -24.3 | -22.5 | 7% |
| 25.70 | -26.2 | -27.4 | -26.7 | -26.8 | 2% | 39% | 25.70 | -18.6 | -19.3 | -21.6 | -19.8 | 8% |
| 21.23 | -23.4 | -24.3 | -23.8 | -23.8 | 2% | 40% | 21.23 | -16.2 | -17.0 | -19.2 | -17.5 | 9% |
| 17.44 | -20.9 | -21.4 | -21.1 | -21.1 | 1% | 40% | 17.44 | -14.2 | -15.1 | -17.1 | -15.5 | 10% |
| MIN | -59.9 | -63.5 | -61.4 | -61.6 | 3% | 5% | MIN | -59.3 | -58.7 | -57.9 | -58.6 | 1% |
| PEAK FREQ | 371.1 | 371.1 | 371.1 | 371.1 | 0% | 0% | PEAK FREQ | 459.0 | 459.0 | 371.1 | 459.0 | 11% |
| LFN | 371.1 | -59.9 | -63.5 | -61.4 | -61.6 | 3% | 5% | | 371.1 | -59.1 | -58.4 | -57.9 | -58.5 | 1% |
| BLANK | 459.0 | -59.5 | -63.0 | -60.9 | -61.1 | 3% | 4% | | 459.0 | -59.3 | -58.7 | -57.8 | -58.6 | 1% |

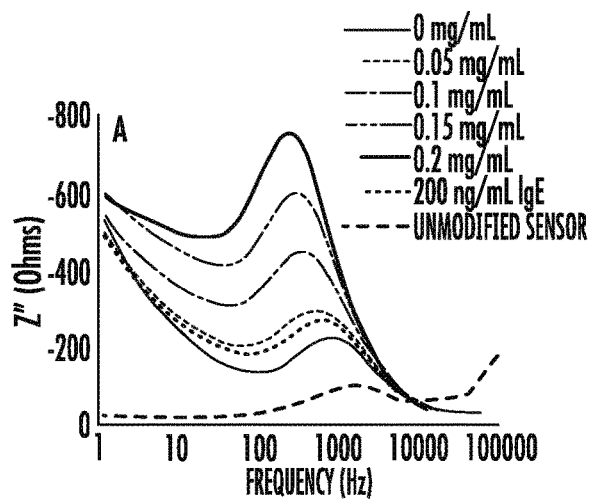
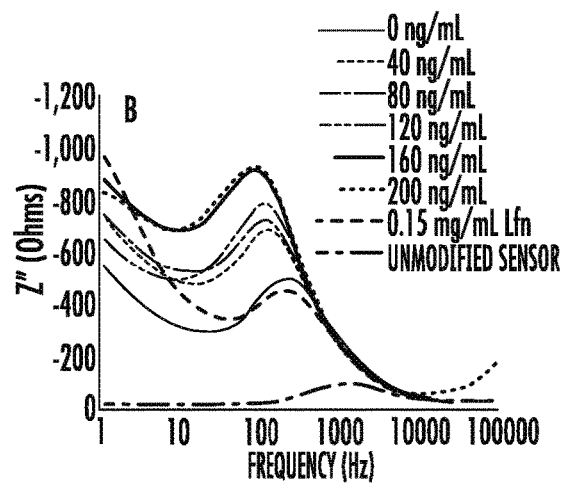
FIG. 20a    FIG. 20b
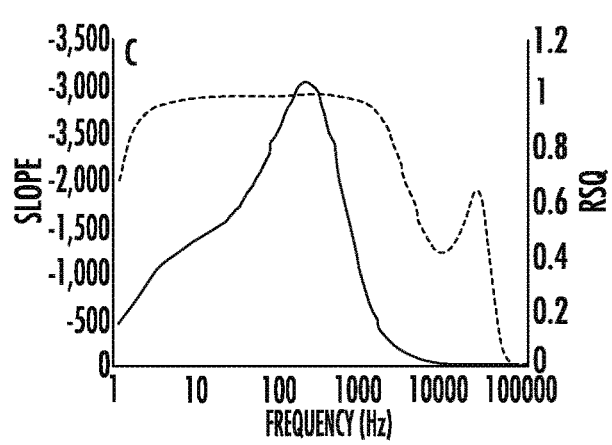
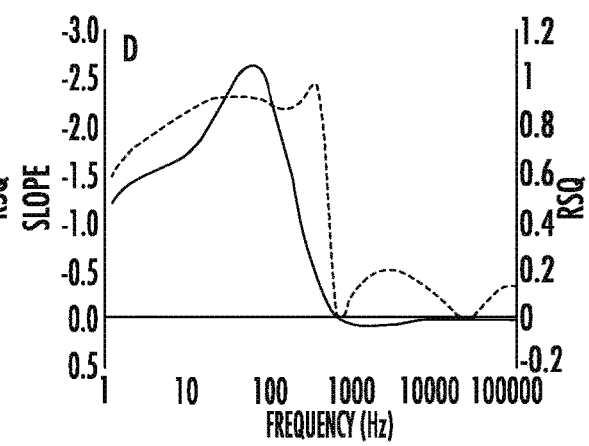
FIG. 20c    FIG. 20d
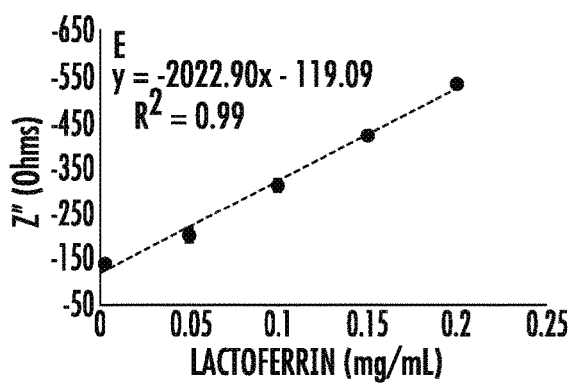
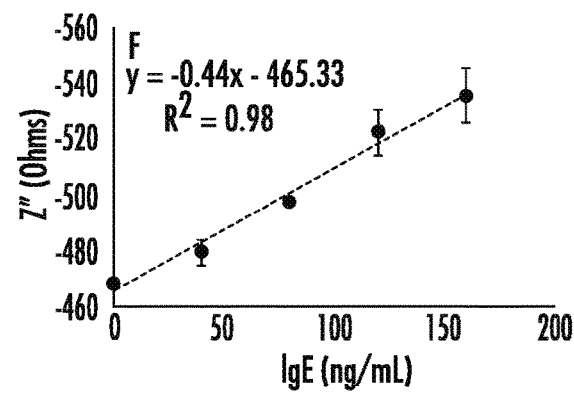
FIG. 20e    FIG. 20f

US 11,714,083 B2

POINT-OF-CARE APPARATUS AND METHODS FOR ANALYTE DETECTIONS USING ELECTROCHEMICAL IMPEDANCE OR CAPACITANCE

CROSS-REFERENCE TO RELATED APPLICATIONS

This application claims priority from the U.S. Provisional Patent Application No. 62/505,004 filed on May 11, 2017, the disclosure of which is incorporated herein by reference.

TECHNICAL FIELD

This disclosure is related to detection tools, diagnostics and related methods involving the use of an electrochemical sensor in conjunction with electrochemical impedance spectroscopy or electrochemical capacitance spectroscopy.

BACKGROUND

Many different analyte detection devices and systems exist. However, those that can be practically applied in a clinical, point of care or other setting requiring accuracy and reliability are fairly limited and tend to be complex and expensive.

SUMMARY

Embodiments herein relate to apparatus, systems, and methods for analyte detection and diagnosis. The presence of biomarkers or other analytes can be detected in bodily fluids, such as tear fluid, saliva, urine, feces, serum, blood, plasma, broncho-alveolar lavage fluid, tissue and cerebral spinal fluid, using Electrochemical Impedance Spectroscopy (EIS) or Electrochemical Capacitance Spectroscopy (ECS), in a handheld point-of-care device, as well as in systems and methods that utilize EIS and/or ECS in combination with a molecular recognition element (MRE) (e.g., a synthetic antibody or bio-mimetic polymer, such as a peptoid) or other target-capturing molecule (e.g., a naturally occurring antibody) on the working electrode of an electrochemical sensor. Such MRE's and target-capturing molecules may include without limitation antibodies, enzymes, receptors, ligands, antigens, DNA, RNA, peptides, and oligomers.

In some embodiments, following perturbation of an electrochemical sensor with an alternating current voltage applied at a discrete frequency, complex impedance, real impedance, imaginary impedance and/or phase shift are utilized to measure the presence or concentration of an analyte.

In some embodiments, the investigation of native optimal frequencies (OFs) revealed a correlation between the native OFs (57.44 and 371.1 Hz for Lfn and IgE, respectively) and the molecular weight of the antibody-antigen complex. Impedance responses at the native OFs have enabled detection limits of 0.05 mg/mL and 40 ng/mL for Lfn and IgE, respectively, covering the clinically relevant ranges. The native OFs were found to be robust across various testing mediums and conditions.

These and other aspects will be described in more detail in the drawings and description that follow.

BRIEF DESCRIPTION OF THE DRAWINGS

FIG. 7 depicts a subset of data from an imaginary impedance approach to analyte detection through EIS after scanning from 1 to 100,000 Hz at a formal potential of 0.1V and an AC potential of 5 mV. In this case, six sensors were loaded with 0.9 microgram of lactoferrin antibody. Three sensors were then exposed to lactoferrin antigen in phosphate buffered saline (PBS) and three sensors were exposed to PBS alone.

FIG. 8 depicts a subset of data from a phase shift approach to analyte (lactoferrin) detection through EIS.

FIGS. 20a-20f show an imaginary impedance (Z") response of Lfn (A) and IgE (B) on the SPCE-alpha platform. Slope and RSQ overlays to determine native OFs of Lfn (C) and IgE (D). Purified calibration curves at each biomarker's optimal frequency Lfn (E) and IgE (F). The linear response across the physiological range of each analyte, can be described by the equations shown in (E) and (F). Each concentration was replicated 5 times.

DETAILED DESCRIPTION

Embodiments herein relate to apparatus, systems, and methods for analyte detection and diagnosis using Electrochemical Impedance Spectroscopy (EIS) or Electrochemical Capacitance Spectroscopy (ECS) in combination with an MRE antibody or other target-capturing molecule on a working electrode.

Embodiments herein further relate to (i) the existence of a biomarker's native OF via direct measurement of biomolecules and (ii) the potential to overcome the limitations in physical adsorption-based immobilization with EIS. Physical adsorption is achieved through glutaraldehyde (GA) mediated cross-linking of MREs on screen printed carbon electrodes (SPCEs). The resulting stability and performance of the sensor in complex media are also evaluated. After building the testing platform, an integrated, disposable tear Lfn and IgE POC test strip prototype was accomplished.

As used herein, an analyte's native optimal frequency is generally accepted as the label-free electrochemical impedance spectroscopy (EIS) response that best reflects the binding of the analyte to its molecular recognition element (MRE). A non-native optimal frequency is measure of a systematic frequency when, for example, a long self-assembled monolayer is used on the sensor surface. Because the monolayer is electrically insulating, it can interfere with the native optimal frequency of the analyte and thus the optimal frequency may not truly represent the native optimal frequency of the analyte, but, rather, more of a systematic optimal frequency that works well for a specific biosensor.

Figure 1A:
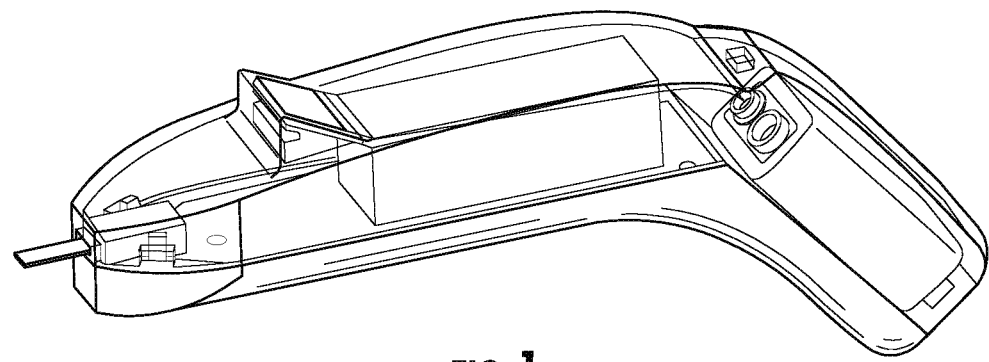
FIGS. 1a & 1b. Form-factor for a point-of-care device embodiment. Designed to fit comfortably in the hand like the currently available products such as the Tono-pen or the iPen, this embodiment features handheld structure with a disposable test strip/sensor that can be easily inserted at the end and then discarded after use. A screen displays the measurement results directly. A OneTouch sensor is attached to show the size of the disposable test strip.
Figure 1B:
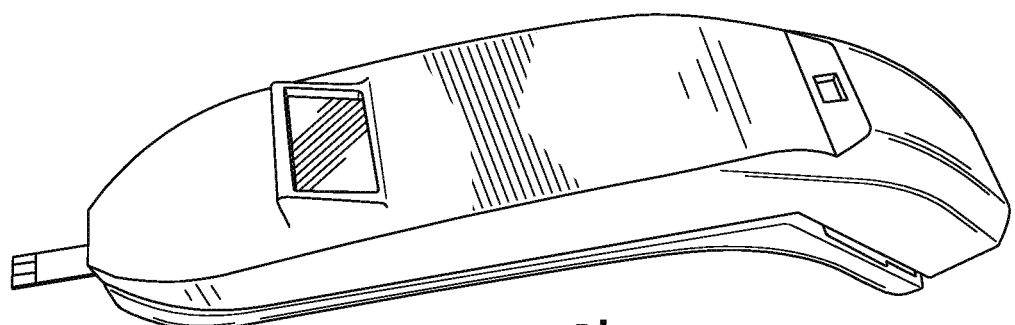
Figure 2:
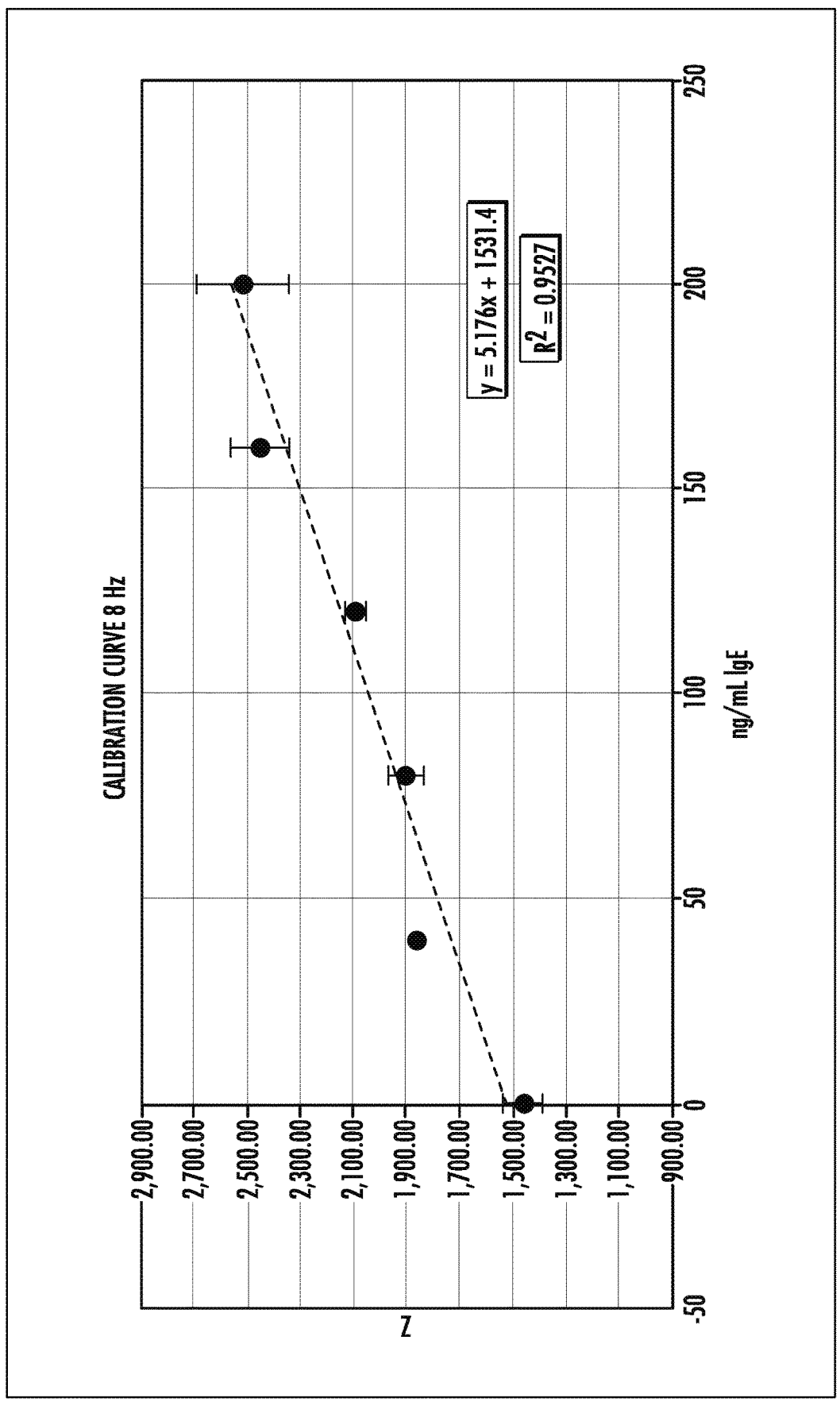
FIG. 2. Electrochemical Measurements. In this case, complex impedance values are measured then the calibration curve equations (samples shown in the figures below) are used to convert the measured impedance to a concentration of an analyte at its signature or at a range of optimal frequencies. The calibration curve equations from linear fits are programmed into the handheld device of FIGS. 1a & 1b to convert measured complex, real or imaginary impedance or phase shift into analyte concentration.
Figure 3:
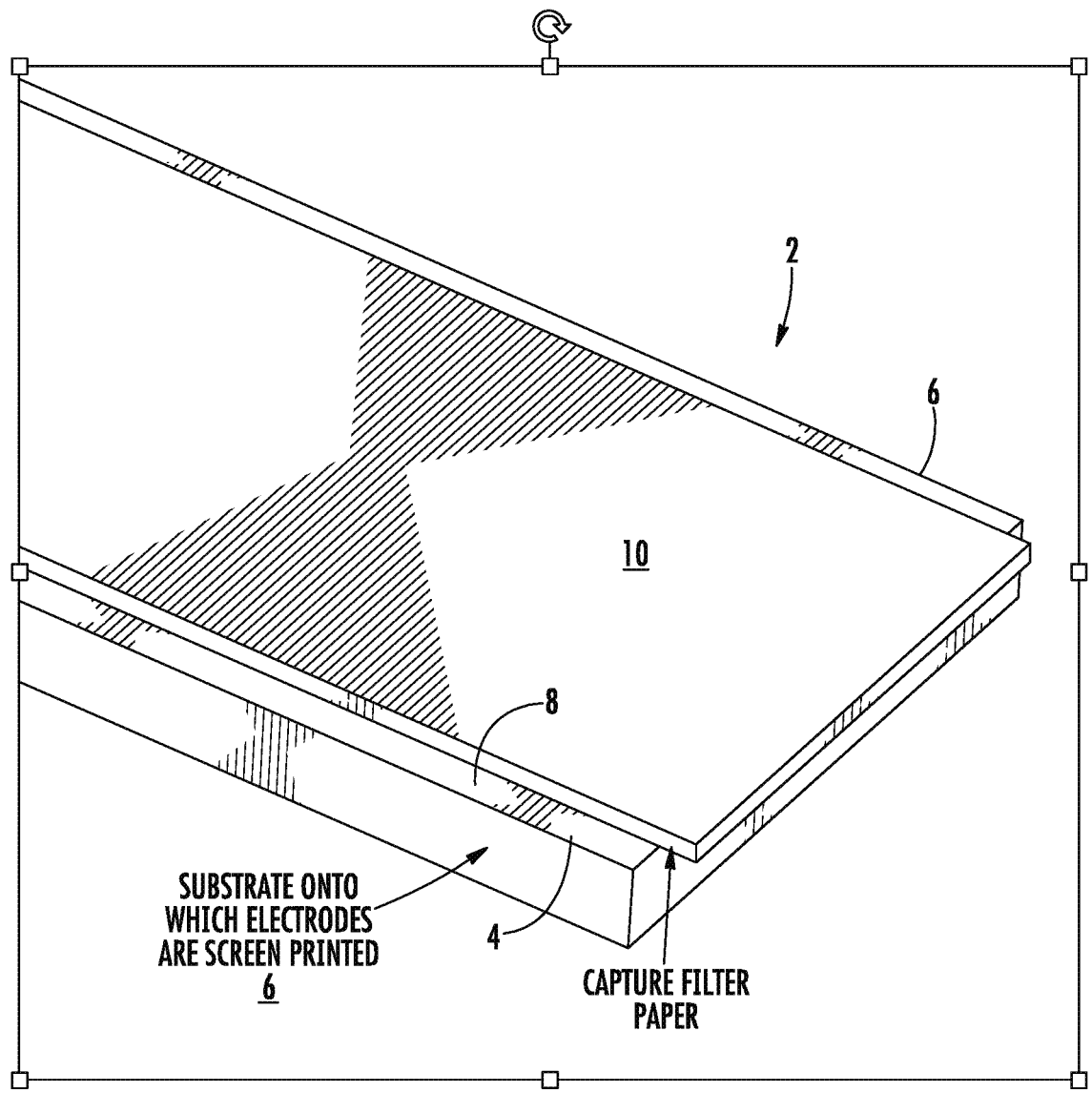
FIG. 3. Sensor Strip Example. In a fluid capture test strip embodiment, a PVC, mylar or similar substrate may be utilized with screen-printed electrode leads (including dried reagents and protein, antibody or other biologic as the target-capturing molecule), and filter paper to absorb tear fluid (with the shape and dimensions of filter paper to be determined based on absorption tests, for example, ~1.75× 1.75 mm. The dimensions of a three-lead electrode are determined based on the filter paper dimensions, with the electrode materials including one or more of carbon conductive ink, silver chloride ink, and novel mesoporous carbon ink and glue, for example, to facilitate electrochemical measurement through a phase shift of a bound complex of a target-capturing molecule and the molecule of interest.

Turning to FIGS. 1 and 3, for example, tear fluid can be drawn to a custom electrode from the eye using filter paper. The presence of biomarkers associated with dry eye can then be detected in the tear fluid using EIS or ECS in a handheld point-of-care device.

For example, as shown in FIG. 3, a sensor strip 2 can be utilized. The sensor strip 2 may include PVC or similar substrate 4 and screen-printed electrode leads 6, which include dried reagents and one or more target-capturing molecules, e.g., an antibody or other protein (together, 8) for subsequent tear assay. In addition to screen-printed leads, the sensor may utilize other methods of electrode fabrication (laser etching, photolithography, sputtering etc.).

Coupled to substrate 4 is an absorbent material, such as filter paper 10, to absorb tear fluid, saliva, urine, feces, serum, blood, plasma, broncho-alveolar lavage fluid, and cerebral spinal fluid with the shape and dimensions of filter paper determined based on absorption tests. For example, the filter paper may be ~1.75 mm×1.75 mm. The dimensions of the electrodes, for example, a 3-lead electrode, are determined based on filter paper dimensions. Electrode materials may include, but are not limited to, carbon conductive ink, silver chloride ink, and novel mesoporous carbon and glue. Mesoporous carbon in combination with, for example, an antibody increases the surface area and permits larger amounts of antibody to be loaded onto an electrode thus improving efficiency of detection.

Figure 4A:
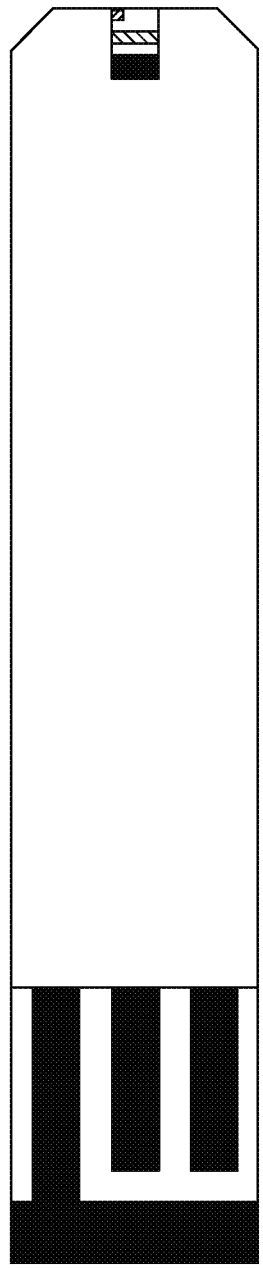
FIGS. 4a & 4b. Sensor Strip Example. The sensor may include between 3-8 layers of screen print inks, each with its own stencil. The complete sensor is shown (right) with a close view of the tip, where the filter paper interfaces.
Figure 4B:
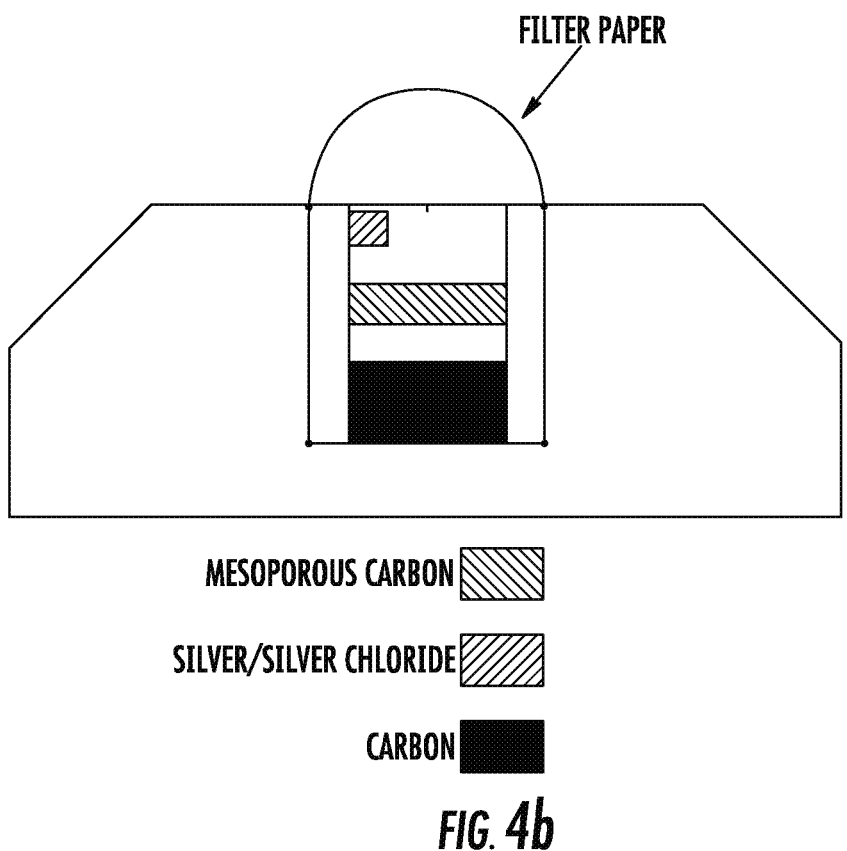
Figures 5A, 5B, 5C, 5D:
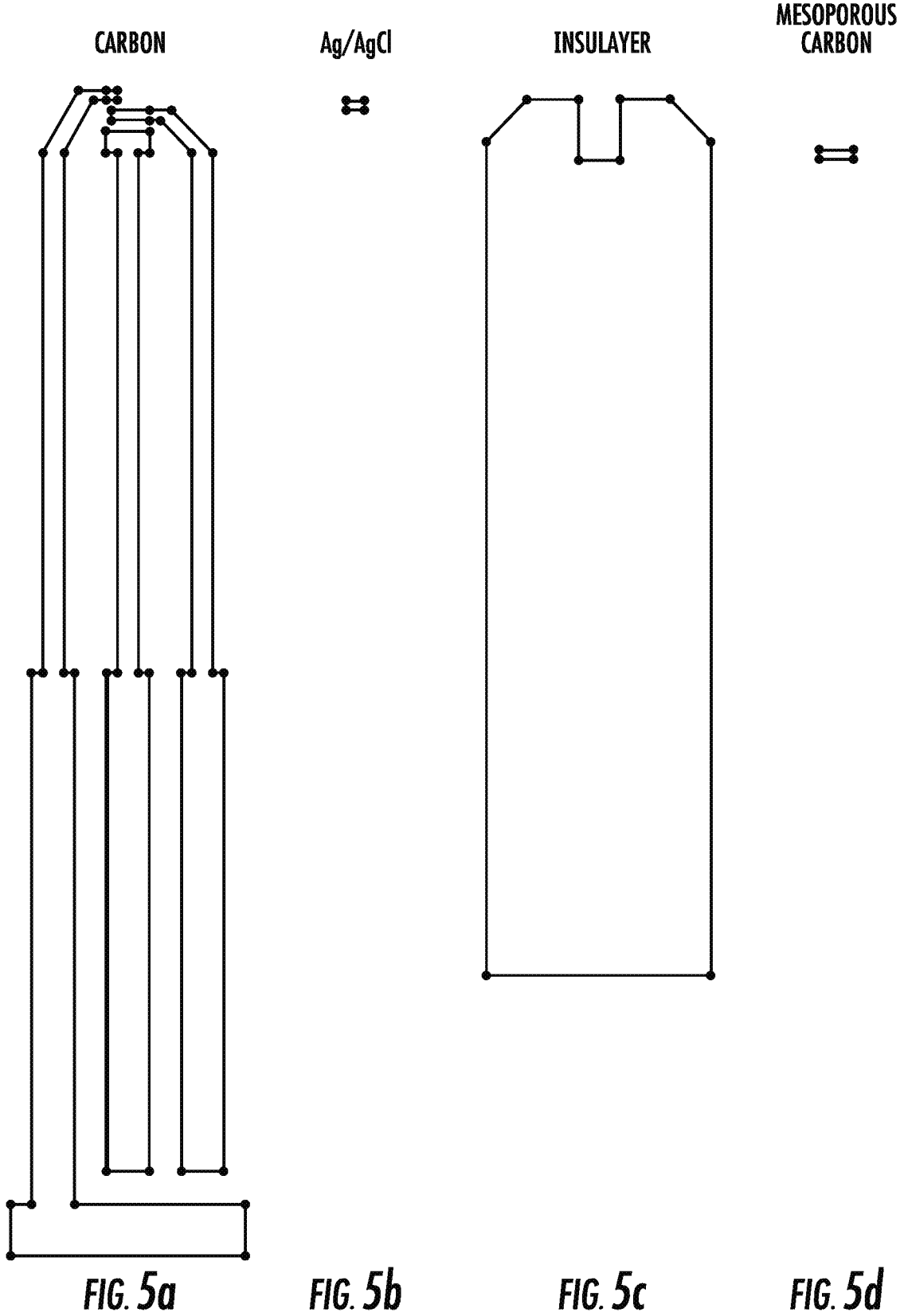
FIGS. 5a-5d. Sensor Strip Electrodes Example. In this embodiment, the four layers of ink are shown as separate stencil designs as they would be printed, the first layer being carbon, then Ag/AgCl2, etc. More or fewer layers, however, can be utilized.
Figure 6:
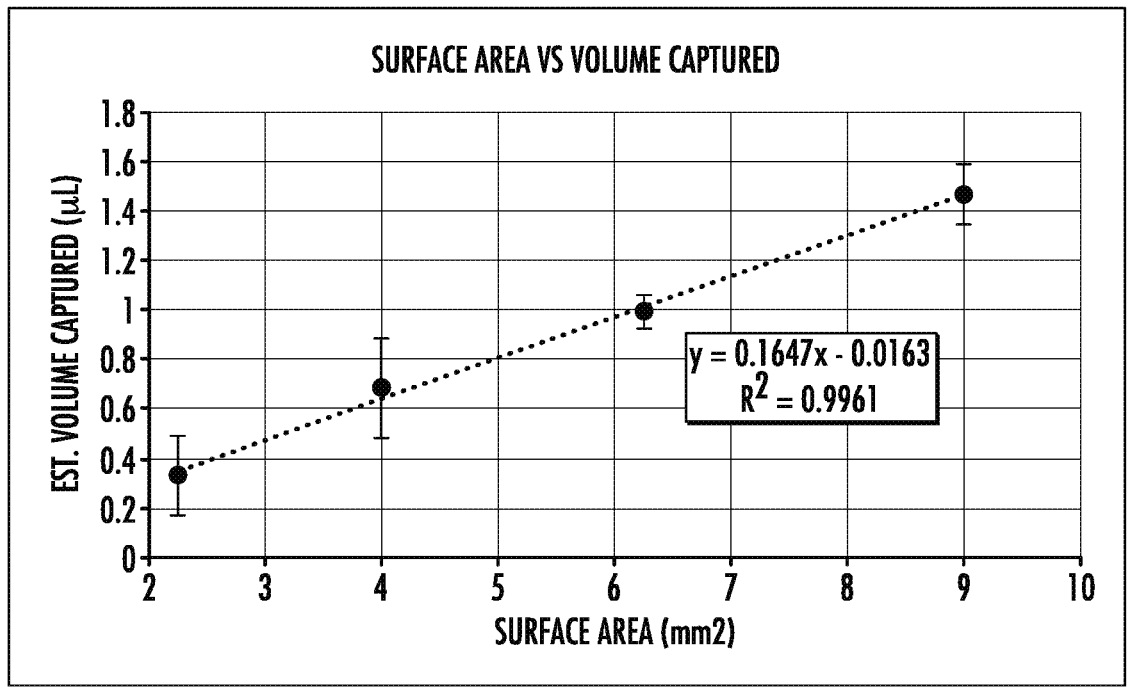
FIG. 6. Sensor Strip Saturation Test. A determination of actual tear fluid volume captured and reproducibility was performed. Four filter paper sizes were measured (n=5) to determine the amount of tear fluid each size can absorb when exposed to a 6 µL pool of tear fluid.

Turning to FIGS. 4a and 4b further examples of a sensor strip is shown. The sensor strip in this embodiment includes 4 layers of screen print inks, each with its own stencil. The complete sensor is shown (right) with a close view of the tip, where the filter paper will interface.

FIGS. 5a-5d depict another sensor strip embodiment. The four layers of ink in this embodiment are shown as separate stencil designs as they would be printed, the first layer being carbon, then Ag/AgCl, then mesoporous carbon, etc.

In summary, sensors have been developed that include one or more target-capturing molecules (for example, antibody immobilized on a working electrode) that have distinct frequency in the bound and unbound states, as well as impedance or capacitance measurements that vary with the amount (concentration) of bound target molecules.

In all sensor embodiments, the sensor would be operably configured to utilize electrochemical impedance or capacitance as a means to generate a calibration line across a range of analyte concentrations. For example, a power supply computer/software, potentiostat, and/or further EIS or ECS components necessary for the sensor to operate/provide measurements are provided.

Thus, the apparatus described herein provides a platform for developing and implementing various electrochemical impedance and/or electrochemical capacitance sensing protocols, apparatus (such as a handheld device), and systems. Accordingly, imaginary impedance and/or phase shift can also be used to detect and quantify analytes of interest in various biological samples.

Figure 9:
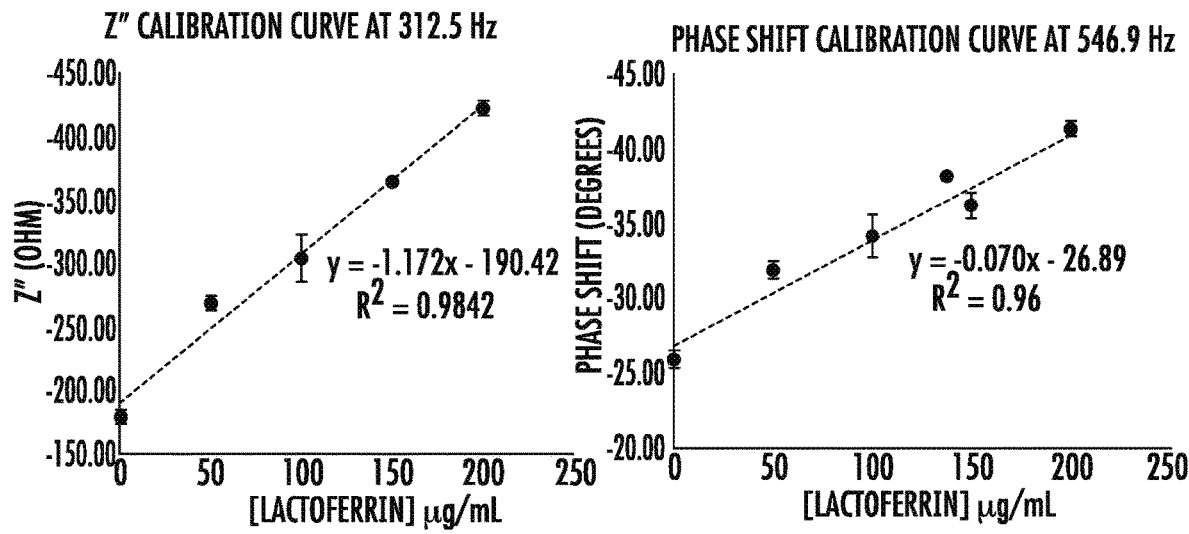
FIG. 9 depicts calibration curves from an imaginary impedance approach (left) and a phase shift approach (right) to analyte detection through EIS.
Figure 10:
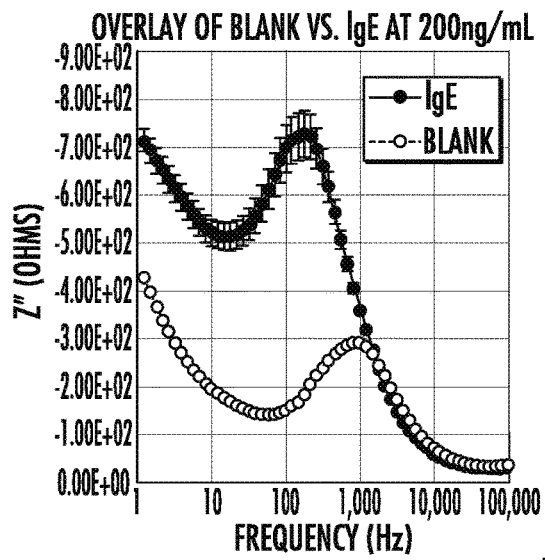
FIG. 10 shows a data overlay of blank versus IgE from an imaginary impedance approach (left) and a phase shift approach (right).
Figure 10:
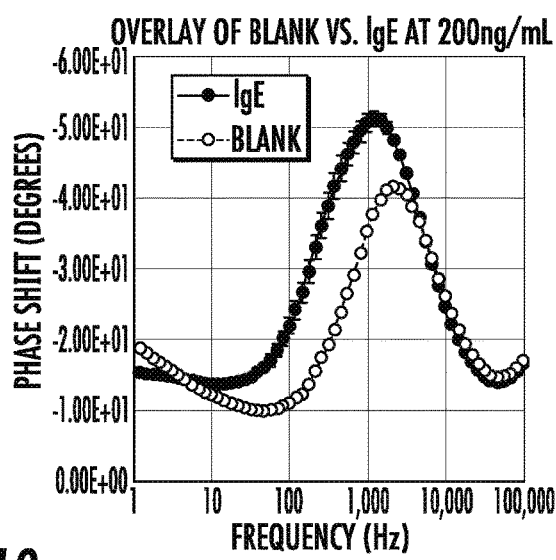

For example, as seen in FIGS. 9 and 10, optimal frequency differ by analyte and method of detection (phase shift θ or imaginary impedance Z"). For Lactoferrin, when using imaginary impedance Z", the optimal frequency is 312.5 Hz. When using phase shift θ, the optimal frequency becomes 546.9 Hz. From these experiments, concentration was found to be linear over therapeutic range (0.5-2 mg/mL) for lactoferrin, while the limit of detection was found to be significantly <1 ng on sensor for IgE.

To improve reproducibility, the inventors have identified an optimal frequency or range of frequencies that is "most robust" against changing variables yet still very specific to target binding (see, e.g., FIGS. 12-17).

Figure 11:
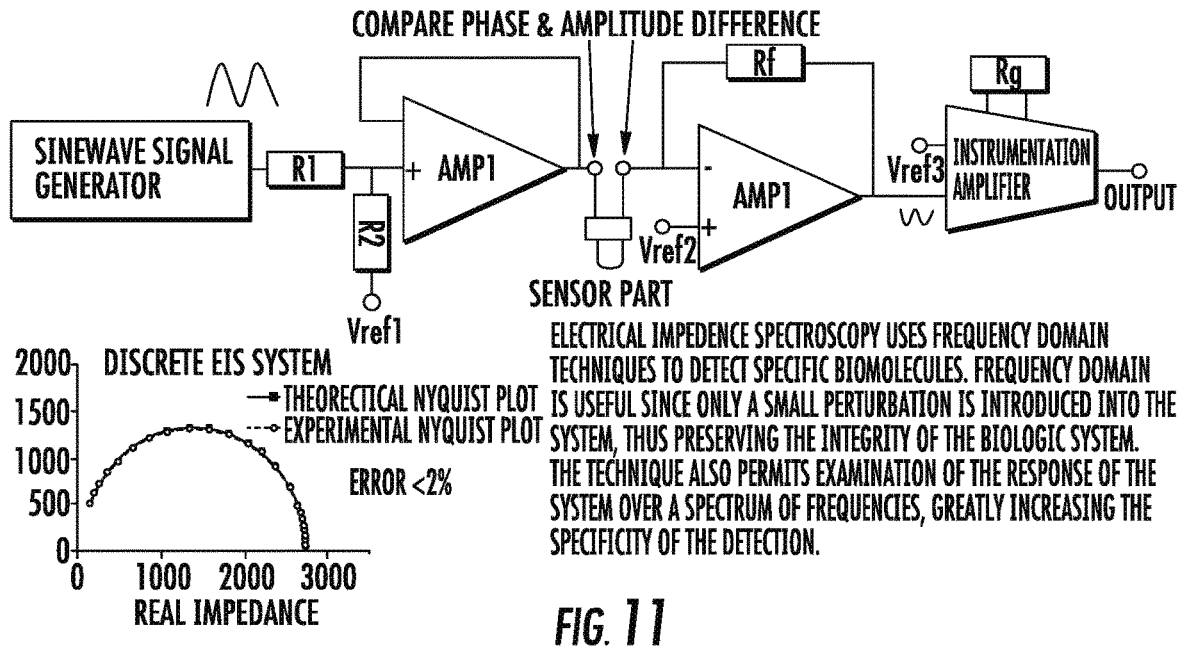
FIG. 11 is a hardware circuit block diagram of a reader configuration utilized with a system of the disclosure.
Figure 12:
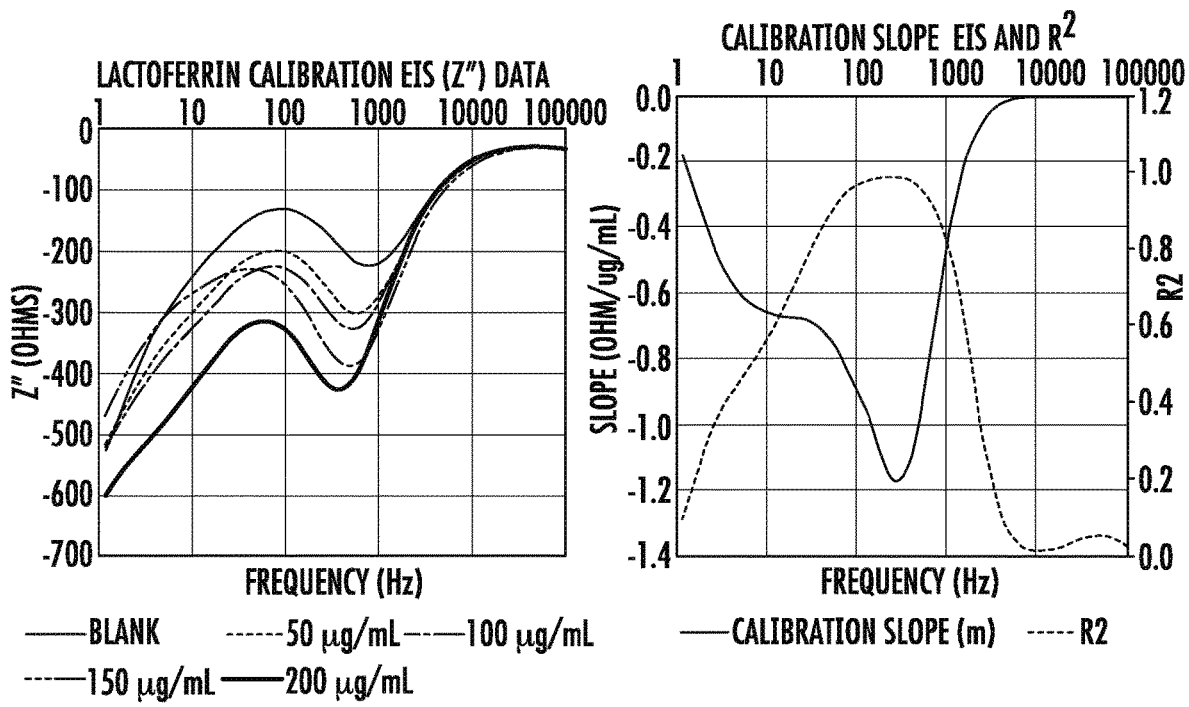
FIG. 12 depicts EIS data (left) after scanning from 1 to 100,000 Hz at a formal potential of 0.1V and an AC potential of 5 mV over a range of lactoferrin concentrations (0-200 µg/mL). The optimal frequency to prepare a quantitative calibration line was found to be around 312 Hz. A plot of $R^2$ and slope against frequency (right) can be used to pick a single frequency or range of frequencies at which to generate a calibration line.
Figure 13:
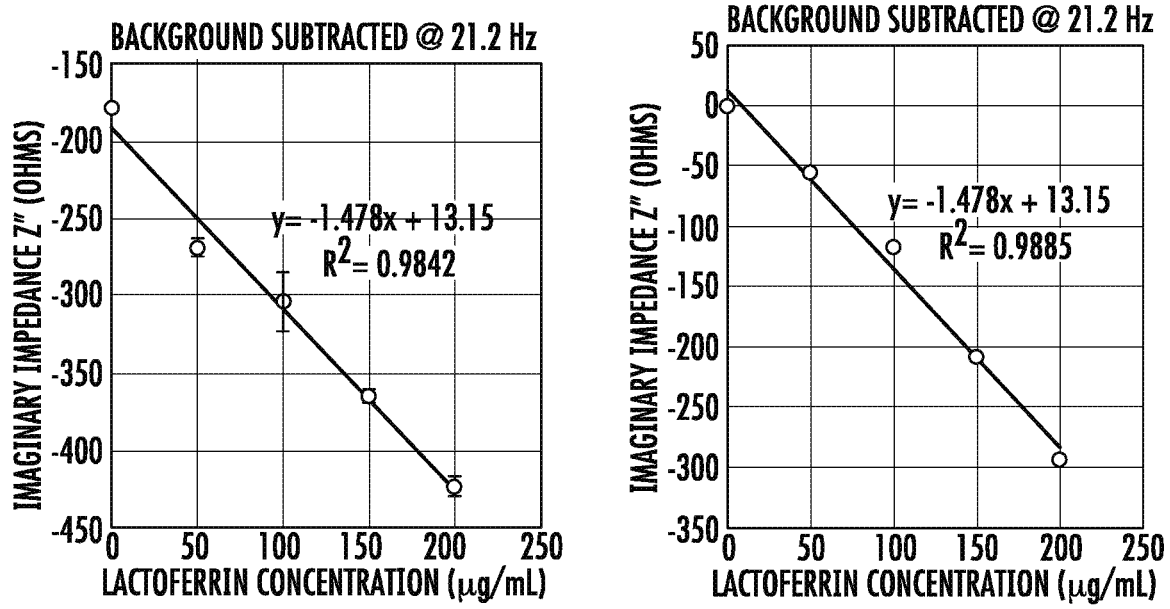
FIG. 13 shows a comparison of original (left) and background subtracted (right) lactoferrin calibration lines at 312 Hz and 21.2 Hz in the form of y=mx+c with $R^2$ values of 0.9842 and 0.9885 respectively.
Figure 14:
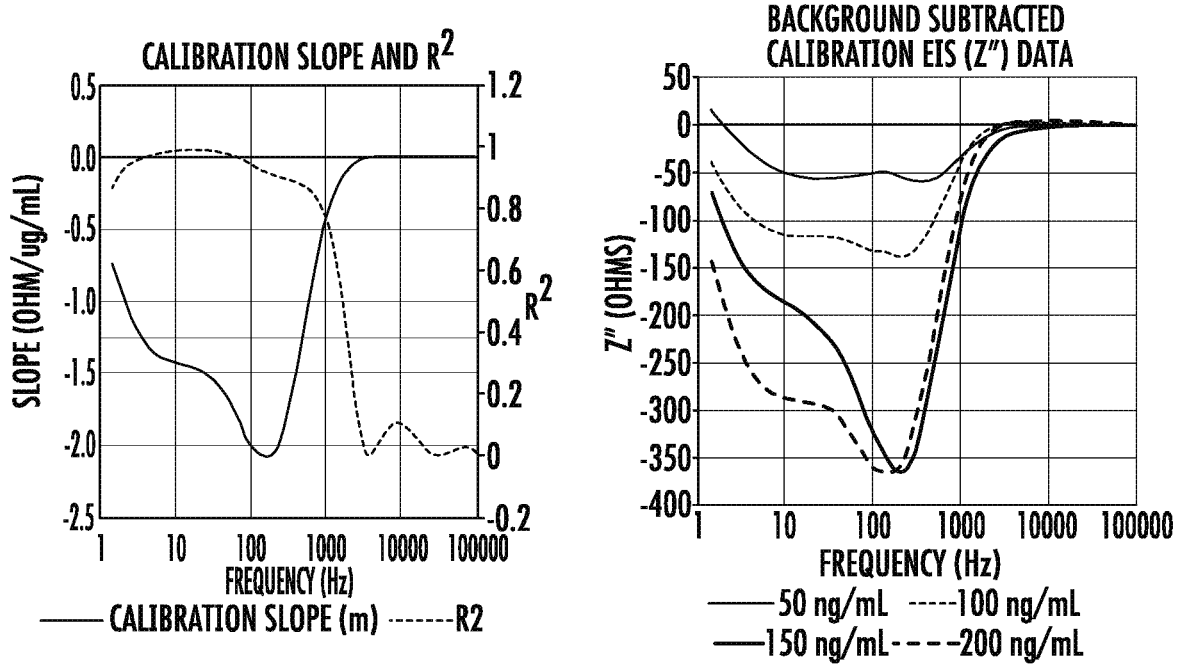
FIG. 14 shows a plot of background subtracted $R^2$ and slope against frequency (left) and background subtracted EIS scans from 1 to 100,000 Hz (right) at a formal potential of 0.1V and an AC potential of 5 mV over a range of lactoferrin concentrations (50-200 µg/mL).
Figure 15:
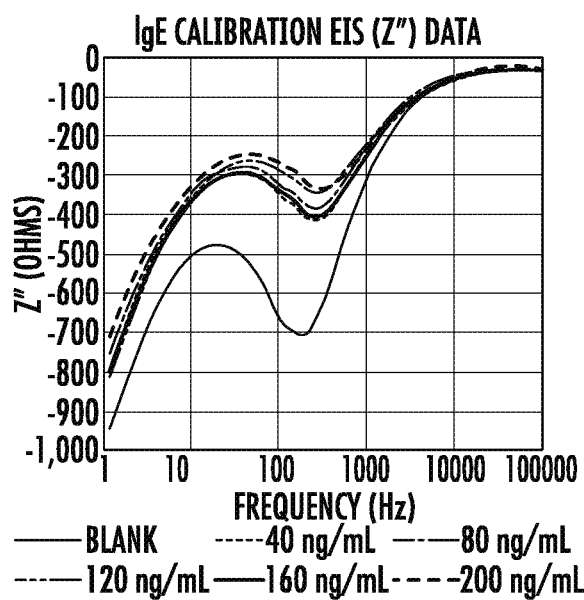
FIG. 15 depicts EIS data (left) after scanning from 1 to 100,000 Hz at a formal potential of 0.1V and an AC potential of 5 mV at a range of IgE concentrations (0-200 ng/mL). Optimal frequency to prepare a quantitative calibration line was found to be around 147 Hz. A plot of $R^2$ and slope against frequency (right) can be used to pick a single frequency or range of frequencies at which to generate a calibration line.
Figure 15:
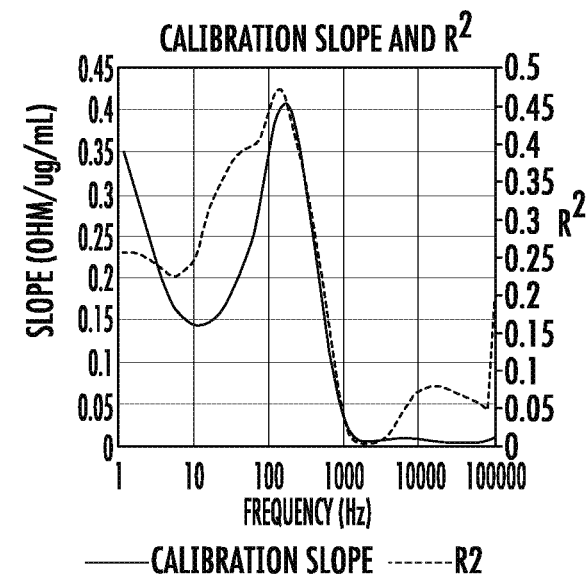
Figure 16:
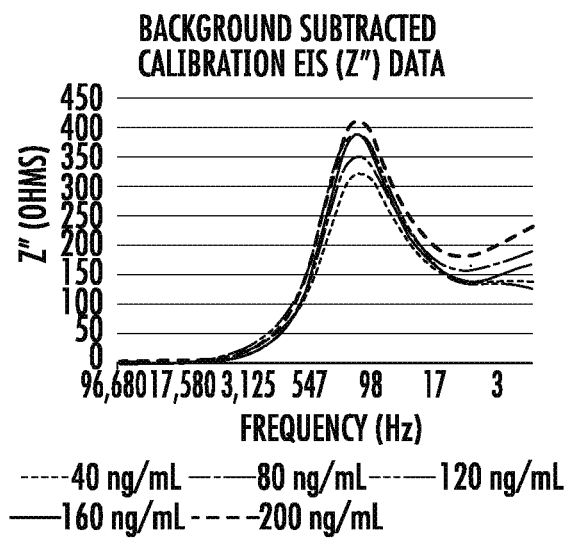
FIG. 16 shows a plot of background subtracted $R^2$ and slope against frequency (left) and background subtracted EIS scans from 1 to 100,000 Hz (right) at a formal potential of 0.1V and an AC potential of 5 mV over a range of IgE concentrations (50-200 ng/mL)
Figure 16:
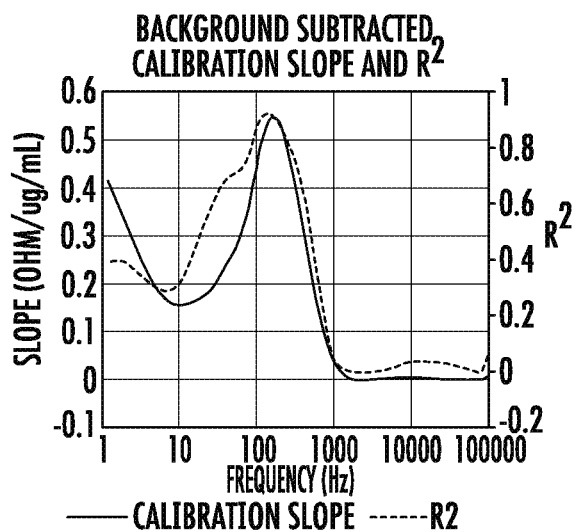
Figure 17:
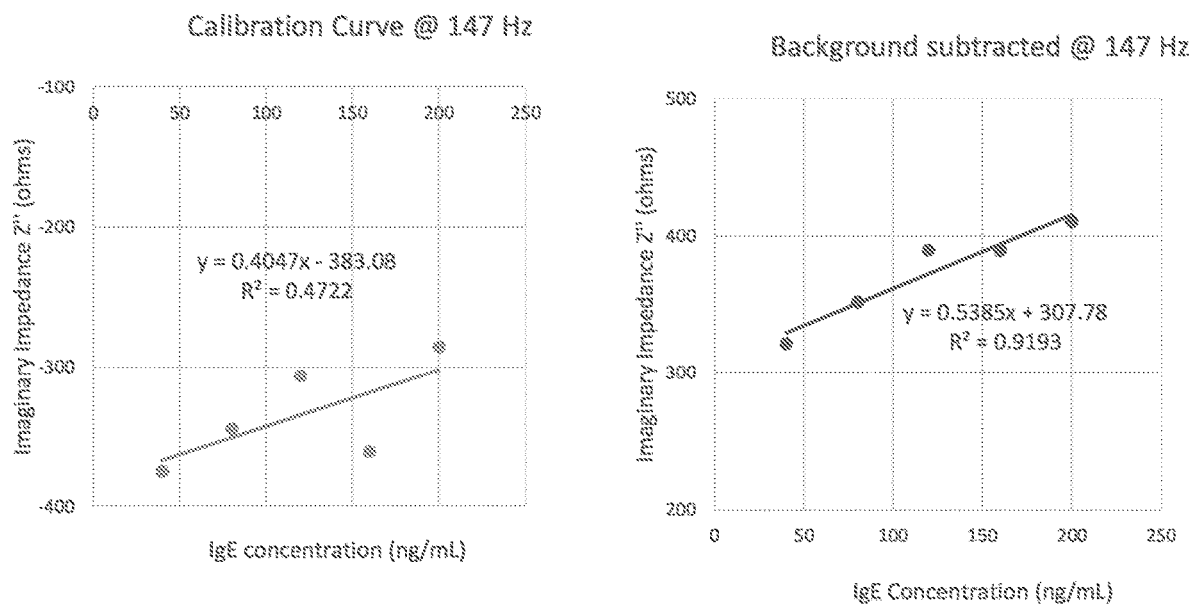
FIG. 17 shows a comparison of original and background subtracted IgE calibration lines. Optimal frequency was found to be 147 Hz.
Figure 18:
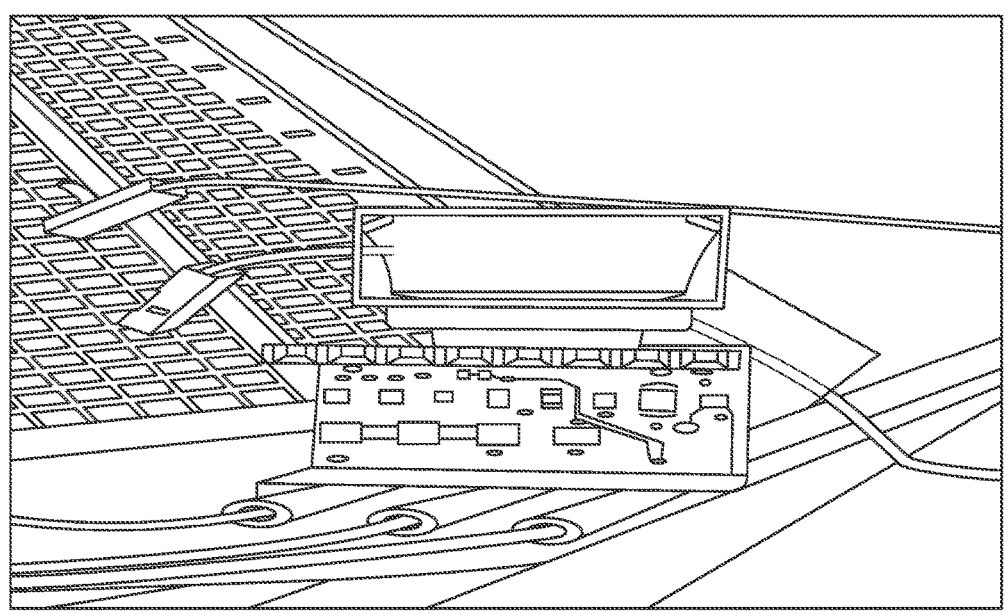
FIG. 18 depicts a layout and design of a radio frequency "reader" for measurement of a target capturing molecule/target complex that uses EIS to generate a low radio frequency voltage at a specific frequency or range of frequencies. The reader thus detects electrical impedance in an electrochemical assay.

In terms of a reader for impedance or capacitance measurements, FIGS. 11 and 18 show a hardware circuit block diagram and a layout and design of a radio frequency "reader" for measurement of a target capturing molecule/target complex that uses EIS to generate a low radio frequency voltage at a specific frequency.

Figure 26:
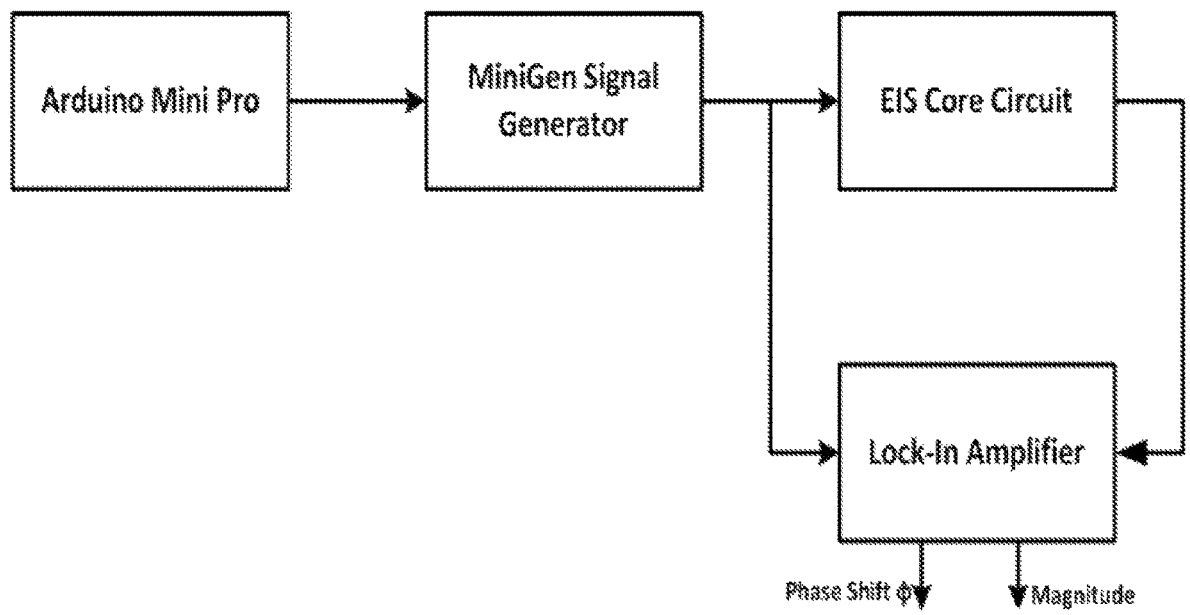
FIG. 26 shows a representative block diagram of an electrochemical impedance spectroscopy (EIS) system as described herein.

In an embodiment, an electrochemical impedance spectroscopy (EIS) system is designed using electrical discrete components as shown in block diagram in FIG. 26.

For example, an Arduino Mini Pro board and MiniGen Signal Generator board have same form factor in size and they overlap on each other due to compatible pin configuration, which further reduces the size of electronics. An Arduino Mini Pro board is programmed to communicate with MiniGen Signal Generator board and generate a sine wave. Then, an EIS core circuit converts down this sine wave signal to appropriate amplitude and formal potential which serves as an input excitation signal to the cell (or the sensor part). Once the sensor returns the signal (aka the output current), it is converted in the same EIS core circuit. The returned signal (output signal) is then compared to the input signal and the phase shift and magnitude of the signal are then converted to analyte concentration by a predetermined algorithm. The results are then displayed on a screen that is operably connected to the other reader components.

Non-Limiting Method Examples

Tear Fluid Example

First, tear fluid is collected. Only the filter paper attached to a test strip briefly contacts the edge of the eye proximal to the lower lacrimal lake to obtain ≤0.5 μL of tear fluid. The device is designed to facilitate tear collection in a quick and ergonomic fashion. The device can then make a sound when enough tear fluid is captured thus signaling that the handheld can be removed from the eye region.

Next, tear fluid is analyzed. The tear fluid on the filter paper wets the electrodes which perform electrochemical impedance or electrochemical capacitance measurements. These electrochemical measurements are converted to an analyte concentration based on pre-programmed calibration curves. For example, if the output signal is Y, then using Y=mx+b, where m and b are known constants and x is the concentration being solved. Then once Y is measured, x can be calculated easily. Next, the concentration can be displayed on a reader for the ocular analyte of interest, which may include, but are not limited to, IgE, lactoferrin, osmolality measurements, MMP9, adenovirus, glucose and/or any molecule to which an antibody exists and which can be immobilized onto the working electrode of an electrochemical sensor.

Figure 27:
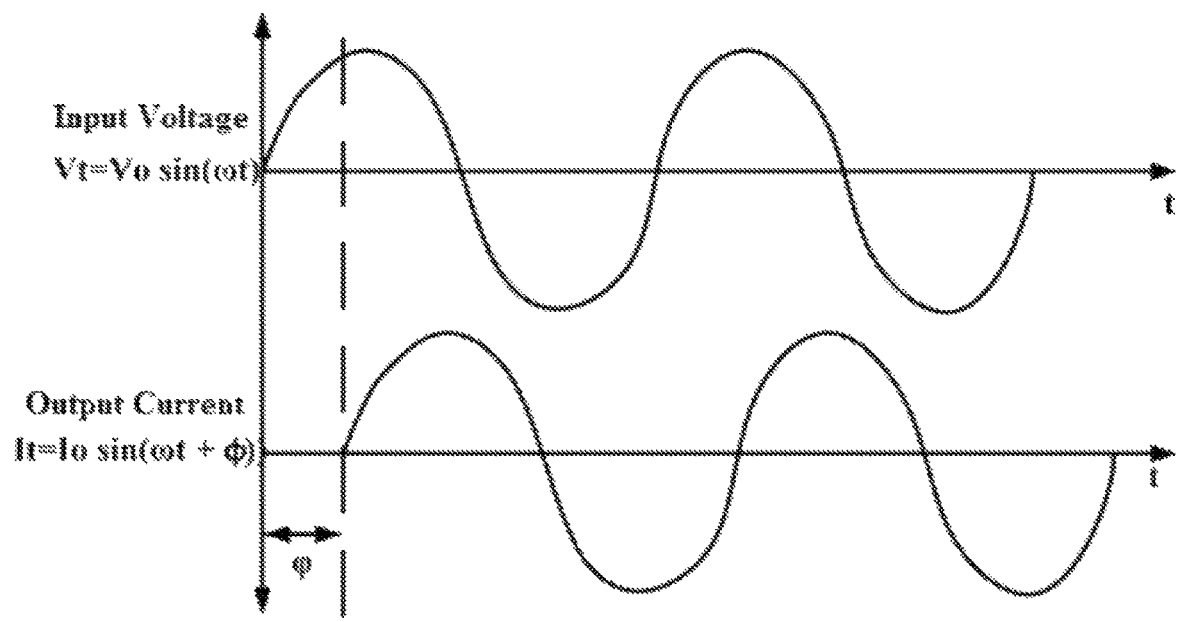
FIG. 27 shows a representative illustration of measurement of electrochemical impedance of an electrochemical cell.

By way of additional example, to measure the electrochemical impedance of an electrochemical cell, an AC potential is applied as an input and the current passing through the cell is measured (FIG. 27). If an electrochemical cell exhibits purely resistive impedance then there is no phase shift between input voltage signal and current passing through the cell assuming the input AC potential is sinusoidal in nature. Also, the frequency of both current and voltage waveform will be same. If an electrochemical cell exhibits purely capacitive impedance, then the current waveform will lead the voltage waveform by 90 degree. If an electrochemical cell exhibits purely inductive impedance, then the current will lag the voltage by 90 degrees. In the real world, an electrochemical cell with solution exhibits a combination of resistive, capacitive and inductive impedance.

Input Excitation Voltage signal and current response

Given an input excitation signal in time domain with the form:

$$V_t = V_0 \sin(\omega t)$$

Radial frequency ω can be expressed in terms of frequency f in Hertz as $\omega = 2\pi f$. The response signal is shifted in phase by φ degrees and is given by, $$I_t = I_0 \sin(\theta t + \phi)$$

Where, $I_0$: Amplitude of response current Φ: Phase shift in current response.

A complex impedance is given by dividing instantaneous voltage signal with instantaneous response current.

$$Z = V_t / I_t$$

$$Z = V_0 \sin(\omega t) / I_0 \sin(\omega t + \phi)$$

$$Z = Z_0 \sin(\omega t) / \sin(\omega t + \phi)$$

Such complex impedance is represented in terms of phase shift φ and magnitude $Z_0$. The same impedance can be represented using Euler's relationship as follows:

$$Z(\omega) = Z_0 (e^{j\phi})$$

$$Z(\omega) = Z_0 (\cos \phi + j \sin \phi)$$

From the above expression, impedance can be plotted over the spectrum ω rad/sec (or in frequency Hz) by only measuring two components: magnitude $Z_0$ and phase shift φ.

The results from device or system measurements may be displayed on the reader device and/or an external device such as a phone or computer, and diagnosis of dry eye syndrome and/or other ocular diseases thereby is made conveniently.

Lactoferrin Antibody/Antigen Example

60 μg/mL antibody solution applied to electrode and dried. The electrode is then subjected to gluteraldehyde vapor for 1 hour and the cross-linking reaction is stopped. Lactoferrin antigen is added to 50% of the sensors and incubated at 4° C. for 15 hours. Next, EIS measurements are run from a frequency range of 1-100,000 Hz.

Imaginary impedance and phase shift plotted. When a sensor is made, it has a baseline impedance signal (either phase shift or imaginary impedance), which can vary among batches depending on the variance in fabrication process. Once the blank is subtracted, the remaining signal can be considered as a "normalized" signal. The normalized impedance signal across the frequency spectrum can be compared across batches and a best, resonating frequency can be identified at which the response is always very reproducible at this specific frequency. The response should also correlate to the analyte concentrations.

Figure 19:
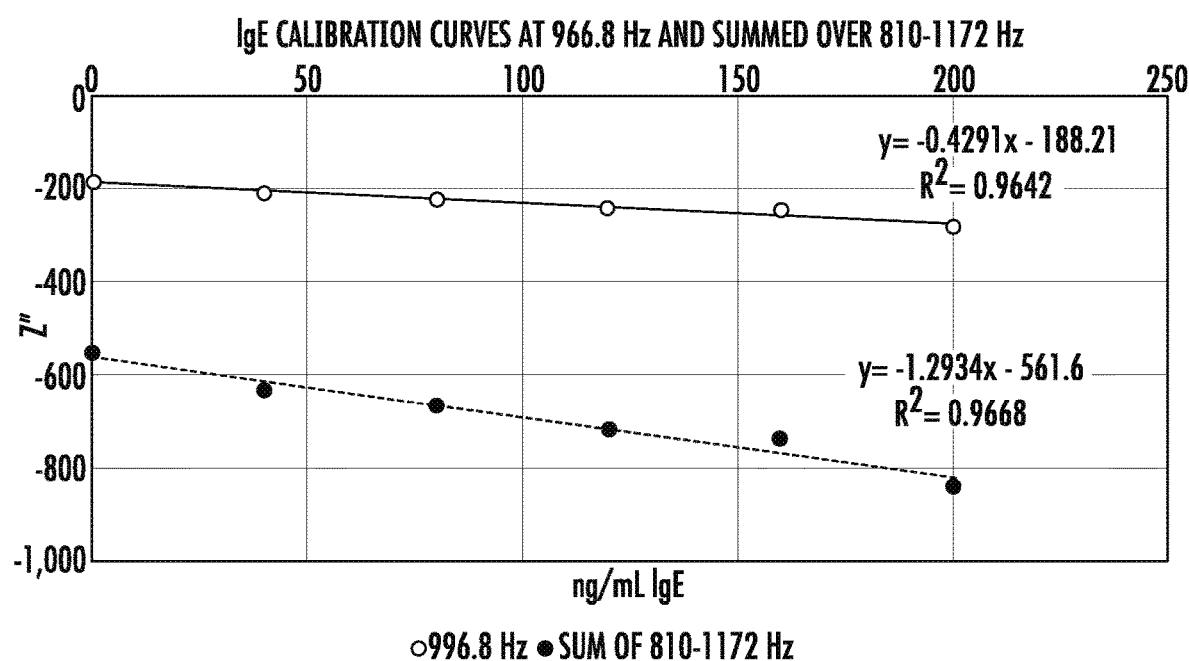
FIG. 19 shows a comparison of a calibration line at a frequency of 996.8 Hz compared with a calibration line summed over the frequency range 810-1172 Hz.

When electrochemical impedance spectroscopy is performed on a sample over 1-100,000 Hz, a dataset featuring measurements of real impedance, imaginary impedance, complex impedance and phase angle is generated for each frequency or range of frequencies studied. A dataset of either real impedance, imaginary impedance, complex impedance or phase angle can either be used to generate a calibration line at a single frequency (FIG. 19, dotted line) or summed to generate a calibration line over a range of frequencies (FIG. 19, solid line).

Measurement of Analyte's Native OF Example

Chemicals and Biologicals. All chemical reagents were purchased from Sigma-Aldrich, MO, unless otherwise stated. The antibodies utilized in the detection of IgE and Lfn were as follows: mouse monoclonal IgG (Scripps Laboratories, CA) and human monoclonal IgG (Fitzgerald, MA), respectively. The IgE antigen supply was obtained from purified myeloma cells courtesy of Scripps Laboratories, CA (lot #2131302) and recombinant human Lfn was obtained from Agennix, TX (lot #803001/803001A). All solutions were prepared in phosphate buffered saline (PBS, pH 7.4) unless stated otherwise.

Preparation of Lactoferrin and IgE Sensor Platforms Screen Printed Carbon Electrodes Setup (SPCE-alpha). The SPCE-alpha was designed for investigating the native OF of a biomarker. This platform was built on a commercially available disposable SPCE, Zensor (CH Instruments, TX), containing graphite working and counter electrodes and a silver/silver chloride reference electrode. First, 1 μg of the respective antibody in PBS was deposited onto the working electrode and dried in a Thermocenter at 24° C. for 25 min. Once dry, the sensors were exposed to GA vapor generated from 1 mL of 25% GA in a parafilm-sealed vessel on an orbital shaker for 1 h at 80 rpm. This process permits covalent cross-linking of the deposited antibodies. The sensors were again dried at 24° C. for 25 min, allowing the cross-linked antibodies to adsorb onto the graphite working electrode. Blocking of unreacted aldehyde groups from GA-cross-linking was achieved by submerging the sensing well in 1 mM Trizma and hydrochloric acid (TRIS-HCl) solution (pH 7.4) for 25 min. Sensors were rinsed in PBS followed by DI and again dried at 24° C. The sensors were either (i) immediately subject to electrochemical testing or (ii) stored at 4° C. for future stability evaluation.

Screen Printed Carbon Electrode with Integrated Tear Sampling Component (SPCE-beta). To expand on the application potential of SPCE-alpha, a tear sampling component (TSC)-integrated form, SPCE-beta, was adopted. Whatman ashless filter paper (Lot #9585790) used in Schirmer's test strips and an adhesive layer (3 M 467MP/200MP, Grainger, AZ) were utilized to construct the TSC. The filter paper and the adhesive layer were cut into their respective shapes using a Universal Laser PLS 4.75 laser cutter. To construct the SPCE-beta, 30 μL of 10 mM potassium ferricyanide (III) was dried onto the sensing well of the prefabricated SPCE-alpha at 24° C. for 45 min. To mount the TSC, the adhesive layer was carefully placed around the sensing well to prevent any contact with the counter, reference, or working electrodes. The filter paper was then attached to the sensor with the adhesive tape. Completed sensors were stored dry at room temperature prior to testing.

Electrochemical Evaluation. All sensors were connected to an electrochemical CHI 660C analyzer (CH Instrument, TX) using a soldered gold-plated edge connector (Digikey, MN). Cyclic voltammetry (CV) was first conducted to determine the formal potentials (input voltage for EIS) of SPCE-alpha and SPCE-beta. CV was performed by sweeping from −0.6 to 0.6 V. EIS was then used as the primary means of evaluation. To conduct EIS, a sinusoidal input voltage with a 5 mV amplitude spanning a range of frequencies from 100 kHz to 1 Hz with a resolution of 12 points per decade was used.

SPCE-alpha. Electrochemical Testing of SPCE-alpha. To conduct CV, 50 μL of 10 mM potassium ferricyanide (III) was added to the SPCE-alpha sensing well. After obtaining the formal potential, all SPCE-alpha EIS measurements were performed by incubating 5 μL of a known antigen concentration for 60 s on the working electrode surface. Next, 45 μL of 10 mM potassium ferricyanide solution was added before initiating the EIS scan. A range of antigen concentrations were tested to cover the desired calibration range for the analyte in question. The clinical cutoffs for Lfn and IgE are 1.1 mg/mL 80 ng/mL, respectively. Empirical testing was performed on the following antigen ranges: 0-0.2 mg/mL and 0-160 ng/mL for Lfn and IgE, respectively. To reduce potential discomfort on dry eye subjects, a 0.5 μL sample volume on the final Lfn sensor was proposed. To accommodate this, the calibration range was intentionally lowered by a factor of 10 to mimic the total mass of Lfn in a 0.5 μL sample. No adjustments were made for IgE as the sample volume for the final IgE sensor is expected to remain 5 μL. All quantitative data is reported as an average signal obtained from 3-5 replicates.

Specificity Testing of SPCE-alpha. Specificity was demonstrated by exposing the anti-Lfn-modified sensors to IgE antigen and vice versa. In these experiments the concentrations of Lfn and IgE were 0.15 mg/mL and 200 ng/mL, respectively, to represent their higher physiological ranges.

Stability Testing of SPCE-alpha. After storing the sensors at 4° C. for 7 days, the sensors were electrochemically tested against 0-0.2 mg/mL and 0-160 ng/mL Lfn and IgE, respectively, to evaluate sensor performance.

Complex Medium Testing of SPCE-alpha. To assess the sensor's performance in a complex medium resembling human tears, a simulated tear recipe containing salts and large proteins was adopted. The simulated tear fluid is made by mixing 2.68 mg/mL lysozyme, 6.5 mg/dL D-glucose, 1.34 gamma globulin, 6.5 mg/mL sodium chloride, 2.68 mg/mL bovine serum albumin, 0.08 mg/mL calcium chloride dihydrate in deionized water (pH 7.4). The solution was used to prepare the antigen concentration gradients immediately prior to testing. The sensors were tested against 0-0.2 mg/mL and 0-160 ng/mL Lfn and IgE, respectively.

SPCE-beta. Electrochemical Testing of SPCE-beta. On average, the SPCE-beta collects 15 μL of fluid with 6% relative standard deviation (RSD) (data not shown) in 20 s. Functional prototypes of TSCs capable of collecting 0.5 μL samples were also investigated, but due to the surface area of the sensing well, a 15 μL volume was the smallest feasible sample volume to avoid shorting. To collect the sample, the TSC of the SPCE-beta was submerged in an excess of antigen solution for 60 s to ensure adequate rewetting of the dried reagents and to permit analyte diffusion through the porous filter paper. An additional 60 s incubation was observed to permit analyte binding to the respective MRE absorbed to the working electrode surface. EIS testing began at t=120 s. The sensors were tested against 0-0.2 mg/mL and 0-160 ng/mL Lfn and IgE, respectively.

Specificity Testing of SPCE-beta. The specificity was validated on the SPCE-alpha and no significant differences were expected with the addition of the TSC.

Complex Medium Testing of SPCE-beta. The functionality in complex medium was validated on the SPCE-alpha and no significant differences were expected with the addition of the TSC.

Determination of Biomarker's Native OF. To determine the native OF of a biomarker, a modified algorithm using the imaginary impedance (Z") response was employed. The Z" values were correlated to target antigen concentrations across the entire frequency spectrum resulting in quantitative descriptors of the calibration line at each discrete frequency, such as slope and R-squared values (RSQ). Unlike other works that advocate the existence of an OF, the native OF is defined as the single frequency at which the RSQ is highest and sufficient slope is displayed. The significance of an OF is described further in the discussion.

Analysis of Sensor Performance. For reproducibility, the error bars are expressed as one standard error, calculated by $\sigma/\sqrt{n}$, where $\sigma$ is the standard deviation of all replicates performed at that concentration, and $\sqrt{n}$ is the square root of the total number of replicates. The limit of quantification (LOQ), is expressed as the lowest amount of analyte in a sample that can be quantitatively determined with suitable precision and accuracy (generally ±20% RSD).

RESULTS AND DISCUSSION

Investigation of Optimal Frequencies Using SPCE-alpha Electrochemical Response of Purified IgE and Lfn. FIGS. 20a-20f display the Z" plotted as a function of frequency over a range of antigen concentrations. FIGS. 20a and 20b show that the Z" trend increases with concentration for both antigens. FIGS. 20c and 20d depict the slope and RSQ response parameters across the frequency sweep. The native OFs for Lfn and IgE have been determined to be 57.44 and 371.1 Hz, respectively. The calibration least-squares best fit lines in FIGS. 20e and 20f are reflective of the sensor response at the native OF. From FIGS. 20a-20d, it is evident that the overall impedance patterns are significantly different between the two biomarkers, confirming that the existence of a native OF is biomolecule-dependent (discussed later).

Assuming the existence of a native resonant frequency describing the binding kinetics between a biomarker and its MRE, it is possible to constructively reinforce the reaction by delivering an input of the same frequency. Therefore, the impedance response of a biomarker at its native OF will be most precise (highest RSQ) as compared to other destructive frequencies.

Figure 21A:
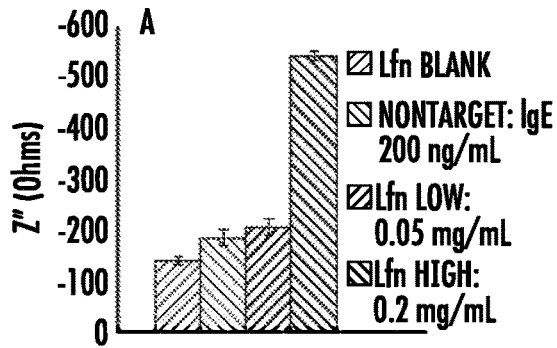
FIGS. 21a and 21b illustrate an assessment of the dynamic range of sensor responses across the physiological range for Lfn (A) and IgE (B), respectively. The signal magnitude generated by purified solutions containing the nontarget analyte is also shown. Each condition was replicated 5 times.
Figure 21B:
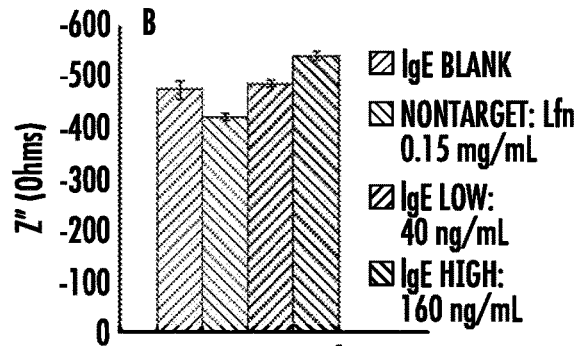

Specificity. The sensor response when subjected to non-target proteins across the frequency spectrum is shown by the interrupted lines in FIGS. 20a and 20b. The specific response at each biomarker's native OF is shown by the nontarget bars of FIGS. 21a and 21b. The Lfn sensor platform was exposed to high concentrations of IgE (200 ng/mL) and vice versa (0.15 mg/mL Lfn). The signals generated from nontarget analytes suggest that the functionalized sensor is specific to the target at each biomarker's native OF. Additionally, it should be noted that the Lfn protein is present at 1000× the concentration of IgE. The minimal resulting signal suggests that the sensors are specific to their target analytes, with limited binding to undesired species. Although the signals from IgE's high and low concentrations (FIG. 21B) are similar to blank, t tests show that statistical difference (P value<0.05) exists among all data points in FIG. 20F except the 120 ng/mL and 160 ng/mL combination. Further optimization of the surface chemistry is required to achieve clinical utility with this sensor. However, the current platform is sufficient for exploring the theory of native OF.

Figure 22A:
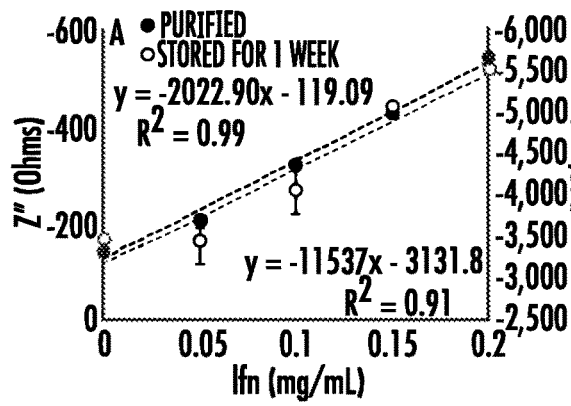
FIGS. 22a and 22b show SPCE-alpha responses in both purified (immediately tested) and one-week storage are shown for Lfn (A) and IgE (B), respectively. Each concentration was replicated 3 times.
Figure 22B:
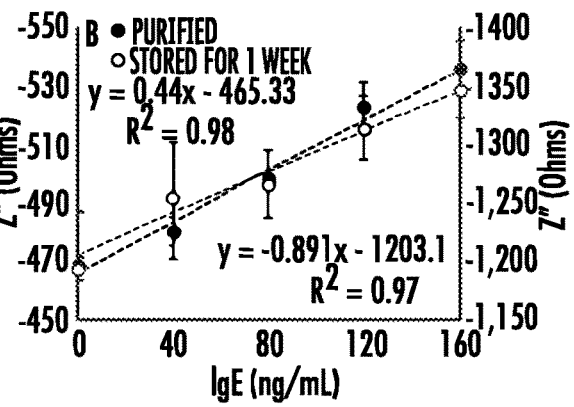

Stability Testing. Given the simple yet crude immobilization approach, stability testing was performed to investigate the retention of biological activity and functionality of the MREs after a specified duration. The calibration lines generated at the native OFs after 1 week of storage at 4° C. are shown in FIGS. 22a and 22b. In comparison to the purified responses, both sensors exhibit increased baseline impedance following storage. This can be explained by the concept of antibody permeation into the pores of the graphite working electrode creating a stronger barrier to electron flow. The increasing impedance magnitude has masked the signal at the lowest antigen concentrations, increasing the LOQ, effectively decreasing sensitivity to low biomarker concentrations. This can be overcome by further optimization of the GA incubation conditions to adjust the degree of MRE cross-linking. Overall, the biological activity is retained after 1 week as supported by the performance similarity to purified responses.

Figure 23A:
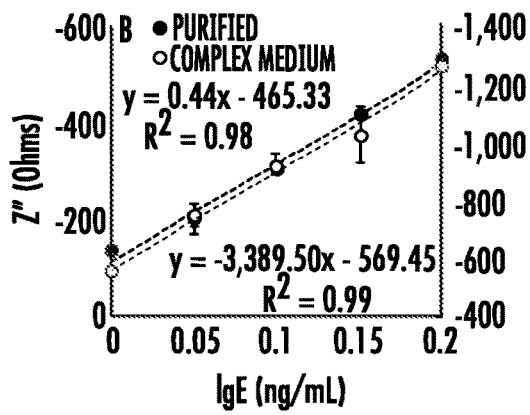
FIGS. 23a and 23b illustrate SPCE-alpha responses in both purified and complex solutions are shown for Lfn (A) and IgE (B). Each concentration was replicated 5 times.
Figure 23B:
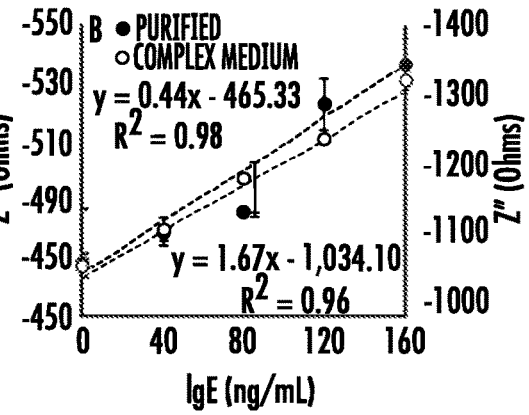
Figure 24:
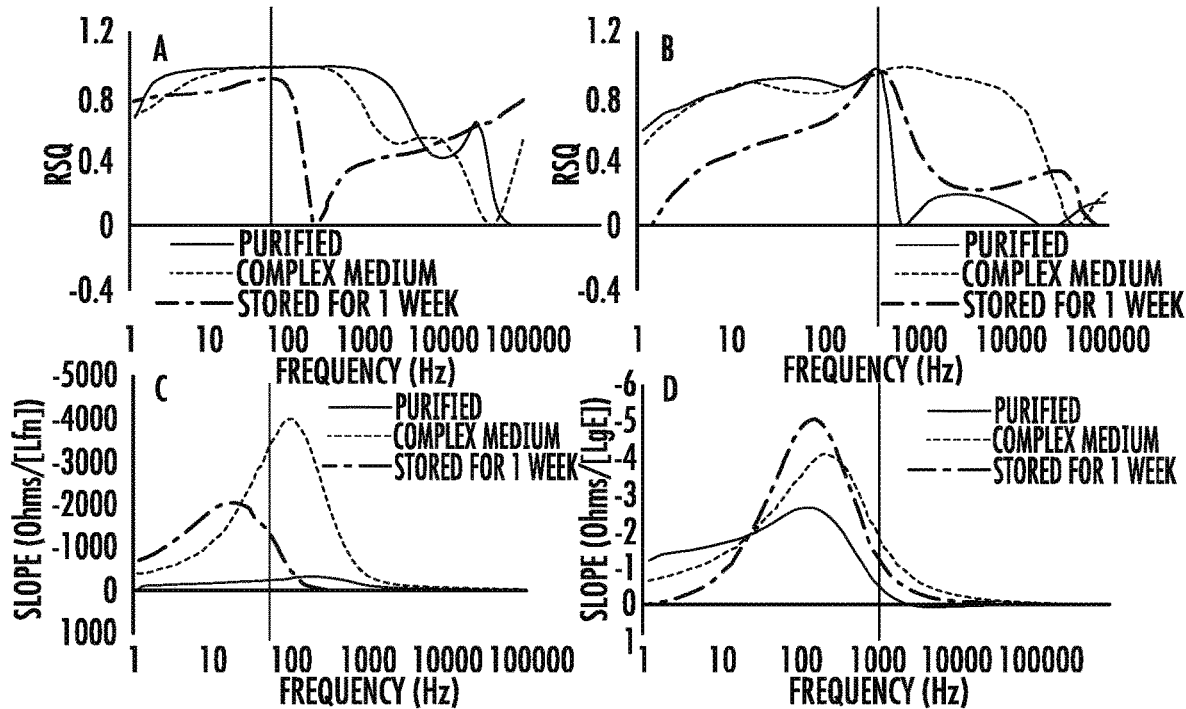
FIGS. 24a-24d show a robustness of native OFs in two mediums of varying electroactive properties (PBS and simulated tears) and after 1 week of storage using the SPCE-alpha platform. The optimal frequencies of Lfn (A,C) and IgE (B,D) remain 57.44 and 371 Hz, respectively, based on RSQ values (shown by vertical lines).

Complex Medium. To evaluate the ability to detect in complex samples, analyte testing in simulated tear fluid was performed using the SPCE-alpha platform. The sensor responses, depicted in FIGS. 23a and 23b, validate the functionality of the platform in the presence of electroactive species and large proteins such as bovine serum albumin, lysozymes, and immunoglobulins. The calibration lines shown in FIGS. 23a and 23b were constructed at each biomarker's native OF. The calculated LOQs for Lfn and IgE sensors are 0.05 mg/mL and 40 ng/mL, respectively, satisfying the clinically relevant cutoff of 1.1 mg/mL and 80 ng/mL, respectively. The reported Lfn sensor detection limit is comparable to other work; however, superior IgE assays surpass the current capabilities of the simplistic, investigational platform described within. Although the slopes vary in comparison to purified samples, the correlations obtained at the native OFs suggest the clinical utility of this platform, and the imaginary impedance algorithm.

Notably, an increase in baseline impedance is present as compared to purified sample responses. This phenomenon can be attributed to the presence of electroactive species and large proteins causing an obstruction to electron flow through the system. Additionally, molecules such as BSA have been previously incorporated into electrochemical applications for their effective blocking capabilities. The nonspecific adsorption of BSA to unabsorbed bare electrode and immobilized antibody is likely to raise the baseline impedance suggesting the need for additional calibration in complex medium prior to sample testing.

The results from FIGS. 20a-20f, 21a and 21b, 22a and 22b, and 23a and 23b also validate the potential of EIS to overcome the well-known weaknesses of physical adsorption-based immobilization. The GA-mediated physical adsorption is a well-studied immobilization technique achieved through primary amine cross-linking, which typically results in loss of antibody activity because of randomized orientation. Unlike other works that utilize GA cross-linking with SAMs, the proposed approach directly immobilizes the antibody complex onto the carbon sensor surface. The reduction in antibody activity from physical adsorption seems to be compensated by the sensitivity of EIS at the native OF, as demonstrated by the retention of high slope and RSQ values. This combination has demonstrated success by achieving clinically relevant detection and shows potential in developing a much faster and simpler immobilization protocol to facilitate mass industrial fabrication.

Robustness of Biomarker's Native OF. To investigate the robustness of a biomarker's native OF, the overlay of slope and RSQ values, under various testing conditions (purified buffer, simulated tears, and 1 week of storage) are presented in FIGS. 24a-24d. The results suggest that although the overall slope values vary with testing conditions, the native OFs remain consistent (vertical lines) as reflected by the RSQ values. This discovery suggests that the determination of native OF should not rely on the response alone, as the OF determined from these methods represent the entire electrochemical cell, which can change depending on the testing medium and other sensor conditions. The native OF should also not be the frequency at which the slope is significantly low. Although previously hypothesized, this is the first report that provides supporting evidence of the existence of a biomarker-specific OF. Further studies at the molecular level are needed to investigate the resonant frequency of a protein, and assess its comparison to the native OF discovered with EIS.

Nevertheless, IgE and Lfn can still be accurately detected in complex medium at each biomarker's native OF. By obtaining the response at a biomarker's native OF, the assay time and hardware requirements for the measuring system can be reduced.

Factors That May Affect a Biomarker's Native OF. OF measurements obtained across different immobilization methods are compared in Table 1. Previously, Lin et al. used SAM-coated gold sensors to immobilize low-density lipoprotein (LDL) and high-density lipoprotein (HDL) antibodies. The algorithm used by Lin et al. to identify the corresponding OF was maximum slope and RSQ greater than 0.95. The resulting OFs for LDL and HDL have been previously identified as 81.38 and 5.49 Hz, respectively. In comparing the LDL and HDL results with this work, it is interesting to note that biomarkers with larger combined molecular weight (antibody-antigen complex) exhibit higher OFs, irrespective of sensor substrate materials and immobilization chemistries. It is also interesting to note that, despite similar combined molecular weights of HDL and IgE antibody-antigen complexes, the reported OFs are hundreds of Hz apart (5.49 and 371.1 Hz, respectively). Although molecular weight is unlikely to be the only factor affecting the native OF of a biomarker, the difference in OFs between HDL and IgE suggests that SAMs can influence the determination of a biomarker's native OF.

TABLE 1

Comparison of the Native OFs of Low Density Lipoprotein (LDL), High Density Lipoprotein (HDL), IgE, and Lfn with Respect to Their Antigen Size, Antibody Size, Association Constant, And Dissociation Constant

| Immobilization Chemistry | Lin et al. SAM with EDC/ NHS coupling | | This Work GA-mediated physical adsorption | |
|---|---|---|---|---|
| Biomarkers | LDL | HDL | IgE | Lfn |
| Optimal Frequency (Hz) | 81.38[7] | 5.49[7] | 371.1 | 57.44 |
| Target Size (kDa) | 532[43] | 175[43] | 190[a] | 80[44] |
| Antibody Size (kDa) | 150 | 150 | 190[a] | 150 |
| Combined Target-Antibody Size (kDa) | 662 | 325 | 340 | 230 |
| Associaton Constant ($M^{-1}$) | $1.3 \times 10^{1043}$ | $2.9 \times 10^{1043}$ | $3.0 \times 10^{10a}$ | $3.3 \times 10^{844}$ |
| Dissociaton Constant (M) | $7.7 \times 10^{-11}$ | $3.5 \times 10^{-11}$ | $3.3 \times 10^{-11a}$ | $3.0 \times 10^{-9 44}$ |

[a]Obtained from manufacturer's specification sheet

On the other hand, the association and dissociation constants do not hold the same correlation across both platforms. Immobilization strategies and chemistries interact with the antibodies on a molecular level. Randomized immobilization, such as the GA cross-linking method, can affect the kinetics of antigen binding sites, altering the association and dissociation constants to a greater extent than site-directed immobilization techniques.

Figure 25:
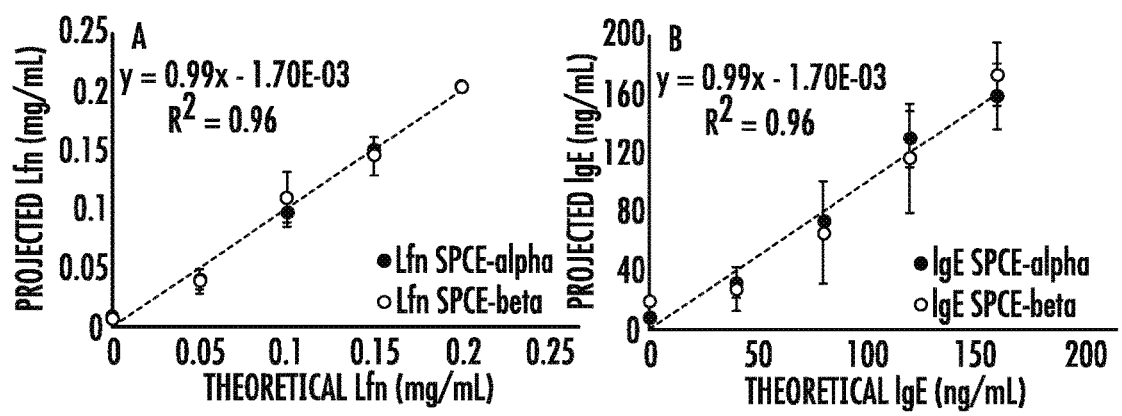
FIGS. 25a and 25b illustrate a linear regression comparing the platform projected response to the theoretical analyte concentration for both biomarkers Lfn (A) and IgE (B). The error bars represent one standard error. Each concentration was replicated 5 times.

Transforming the Testing Platform to a POC Sensor Prototype (SPCE-beta). Electrochemical Evaluation. After verifying the specificity and stability of the sensor using SPCE-alpha platforms, the TSC was integrated to form the SPCE-beta, a large-scale prototype for the proposed POC application. FIGS. 25a and 25b show the projected antigen concentrations by each respective calibration line for the SPCE-alpha and beta platforms, at each biomarker's native OF. The response of SPCE-beta is similar to that of SPCE-alpha, suggesting its capability in predicting analyte concentrations.

Significance of the Integrated Sensor. The integration of TSCs onto a disposable sensor platform is a major improvement to the field of ocular diagnostics. Typically, the collection of tear samples is done using either glass capillary tubes or Schirmer's test strips. By utilizing the same material as a Schirmer's test strip, the safety and substantial equivalency of the TSC for FDA approval is well-supported. A hand-held meter that secures the test strip during sample collection and performs EIS is currently under development.

Schirmer's test strip applications have been thought to cause eye irritation and reflex tearing, causing changes in tear composition and protein concentrations. However, a recent study found that the total amount of protein collected from Schirmer's strip is no different from those utilizing capillary tubes, suggesting that no ocular stress was inflicted. This is perhaps due to more sophisticated manufacturing developments in recent years resulting in enhanced biocompatibility of the paper.

In light of these discoveries, the TSC prototype requires less than 20 s to collect 15 µL of sample. The envisioned final Lfn integrated sensor design will collect 0.5 µL of sample in less than a second, while the final IgE sensor will collect 5 µLin 10 s (data not shown). The required ocular contact time is decreased from the standard 60 s collection time to 1-10 s, promising little to no risk of ocular irritation or discomfort.

The inventors have also considered the potential for sample evaporation when a low (<1 µL) volume is taken. Based on preliminary data, minimal evaporation (<7%) is estimated after 60 s. The amount of evaporation is thus not believed to affect EIS results.

User or patient acceptance of the tear sampling technique is another important consideration in POC ocular diagnostics since stress and irritation can cause variations in concentrations of analytes, thereby increasing result variation. In this regard, Schirmer's test strips are less risky, as capillary tube methods require well-trained personnel and potentially longer contact with the eye. According to one survey, almost all subjects were more apprehensive about rigid glass capillary tubes as compared to flexible filter paper. In addition, samples collected using Schirmer's test strips demonstrated increased reproducibility as compared to those gathered using capillary tubes. After miniaturization, inventors expect the proposed sensors with integrated TSCs to cause minimal stress and irritation, yielding high patient acceptance.

The proposed integrated sensor can also be translated to other diseases whose biomarkers are present in tears. Hagan et al. reported that tear fluid contains many analytes related to diseases in areas as diverse as endocrinology, oncology, the central nervous system, and others. Tear fluid is easily accessible in comparison to blood and requires no sample preparation unlike serum or tissue samples. The proposed integrated sensor, once optimized and miniaturized, will be able to rapidly obtain an accurate biomarker concentration without the inconvenience associated with needle pricking and expensive, complicated test kits. This POC sensor platform is an economical means of screening, diagnosing, and managing many diseases.

Deeper insight has been acquired into the existence of a biomarker's native OF by directly measuring the Z" responses of two example biomarkers using a physical adsorption functionalization method. Inventors have confirmed the robustness of a biomarker's native OF in various testing conditions including complex medium, suggesting its utility as an additional means of detecting specific biomarkers. The OFs may be dependent on the combined molecular weight of the MRE-target complex, and this relationship is upheld across two sensor preparation methods. The inventors have also demonstrated that a sensitive technique, like EIS, can overcome the limitations of simplistic adsorption-based immobilization methods and achieve clinically relevant cutoff values. The transformation of the investigative platform into a practical POC sensor prototype through the novel integration of Schirmer's strip as a TSC, permitting a convenient, quantitative, and rapid sensor for two biomarkers commonly used in differentiating dry eye from ocular allergy, is also shown. The proposed GA-mediated immobilization may benefit from further optimization to make it an attractive technology for clinical use. Future efforts of this work are focused on the optimization and miniaturization of the system for manufacturing purposes and diversifying the range of biomarkers and diseases to which this technology can be adapted.

The claims are not meant to be limited to the materials and methods, embodiments, and examples described herein.

What is claimed is:

1. An apparatus for detecting one or more analytes in a bodily fluid sample utilizing Electrochemical Impedance Spectroscopy (EIS) or Electrochemical Capacitance Spectroscopy (ECS), comprising:
    an electrochemical sensor operably configured to provide an electrochemical impedance or electrochemical capacitance measurement of an analyte in said fluid, said sensor including a target-capturing molecule immobilized to a working electrode in a three electrode configuration, wherein the target-capturing molecule is an antibody, and wherein the antibody is physically adsorbed to the working electrode and covalently cross-linked by exposure to glutaraldehyde, thereby the antibody is directly immobilized onto the working electrode surface in dry form.

2. The apparatus of claim 1, wherein said working electrode comprises one or more of a carbon conductive ink, a silver/silver chloride ink, and a mesoporous carbon ink.

3. The apparatus of claim 1, wherein the sensor is operably configured to utilize electrochemical impedance or electrochemical capacitance to generate a calibration curve across a range of analyte concentration.

4. The apparatus of claim 3, wherein the calibration curve is generated from a dataset of any of real impedance, imaginary impedance, complex impedance, or phase angle.

5. The apparatus of claim 1, wherein the antibody is a lactoferrin antibody or an IgE antibody.

6. The apparatus of claim 1, wherein the working electrode is a screen printed carbon electrode.

7. The apparatus of claim 1, wherein the apparatus is a handheld device.

8. The apparatus of claim 1, further comprising a tear sampling component.

9. A method for detecting one or more analytes in a bodily fluid sample utilizing Electrochemical Impedance Spectroscopy (EIS) or Electrochemical Capacitance Spectroscopy (ECS), comprising:
    contacting said bodily fluid sample with the sensor of the apparatus of claim 1; and
    measuring an electrochemical impedance or capacitance of a complex of said target-capturing molecule of the apparatus and said one or more analytes from said fluid on the working electrode of the apparatus.

10. The method of claim 9, wherein said one or more analytes in said fluid are selected from the group consisting of IgE, Lactoferrin, MMP9, adenovirus, and glucose.

11. A system for detecting one or more analytes in a bodily fluid sample utilizing Electrochemical Impedance Spectroscopy (EIS) or Electrochemical Capacitance Spectroscopy (ECS), comprising:
    the apparatus of claim 1; and
    a reader operably configured to provide an electrochemical impedance or electrochemical capacitance measurement of a complex of said target-capturing molecule of the apparatus and said one or more analytes from said fluid on the working electrode of the apparatus.

* * * * *